(12) United States Patent
Brenzel et al.

(10) Patent No.: US 8,443,808 B2
(45) Date of Patent: May 21, 2013

(54) METHODS AND APPARATUS FOR OCCLUSION OF BODY LUMENS

(75) Inventors: Michael P. Brenzel, St. Paul, MN (US);
Paul J. Hindrichs, Plymouth, MN (US);
Richard G. Cornelius, Wayzata, MN (US)

(73) Assignee: Hologic, Inc., Marlborough, MA (US)

( * ) Notice: Subject to any disclaimer, the term of this patent is extended or adjusted under 35 U.S.C. 154(b) by 534 days.

(21) Appl. No.: 12/532,131

(22) PCT Filed: Mar. 18, 2008

(86) PCT No.: PCT/US2008/057357
§ 371 (c)(1),
(2), (4) Date: Mar. 1, 2010

(87) PCT Pub. No.: WO2008/115922
PCT Pub. Date: Sep. 25, 2008

(65) Prior Publication Data
US 2010/0163054 A1    Jul. 1, 2010

Related U.S. Application Data

(60) Provisional application No. 60/895,707, filed on Mar. 19, 2007.

(51) Int. Cl.
*A61F 6/06*  (2006.01)
*A61F 6/14*  (2006.01)
*A61F 6/02*  (2006.01)
*A61F 5/48*  (2006.01)
*A61F 2/02*  (2006.01)
*A61F 2/00*  (2006.01)
*A61B 19/00*  (2006.01)
*A61B 17/08*  (2006.01)

(52) U.S. Cl.
USPC ........... 128/831; 128/830; 128/833; 128/839; 128/840; 128/843; 128/885; 128/898; 600/29; 600/30; 600/32; 606/157

(58) Field of Classification Search
USPC ................ 128/830–833, 839–840, 846, 885; 623/14.13; 600/29–30, 32; 606/157
See application file for complete search history.

(56) References Cited

U.S. PATENT DOCUMENTS 3,635,223 A   1/1972   Klieman
3,870,048 A   3/1975   Yoon
(Continued)

FOREIGN PATENT DOCUMENTS

EP   1908419 A1   4/2008
EP   07703241.5   2/2011
(Continued)

OTHER PUBLICATIONS

International Search Report for International Application No. PCT/US2008/057357, completed Aug. 16, 2008 and mailed Aug. 22, 2008, 3 pages.

*Primary Examiner* — Michael Brown
*Assistant Examiner* — Brandon L Jackson
(74) *Attorney, Agent, or Firm* — Vista IP Law Group LLP

(57) ABSTRACT

The invention describes methods and apparatus for creating permanent occlusion of body lumens such as the fallopian tubes. The methods and apparatus use non-surgical approaches to deliver permanent implants which create acute occlusion of desired body lumens which resolve to permanent occlusions of the lumens.

8 Claims, 23 Drawing Sheets

U.S. PATENT DOCUMENTS

| | | | |
|---|---|---|---|
| 3,911,923 A | 10/1975 | Yoon | |
| 3,942,407 A | 3/1976 | Mortensen | |
| 3,967,625 A | 7/1976 | Yoon | |
| 3,989,049 A | 11/1976 | Yoon | |
| 4,245,623 A | 1/1981 | Erb | |
| 4,374,523 A | 2/1983 | Yoon | |
| 4,493,319 A | 1/1985 | Polk et al. | |
| 4,606,336 A | 8/1986 | Zeluff | |
| 4,700,701 A | 10/1987 | Montaldi | |
| 4,705,518 A * | 11/1987 | Baker et al. | 623/14.13 |
| 5,035,702 A | 7/1991 | Taheri | |
| 5,095,917 A | 3/1992 | Vancaillie | |
| 5,197,971 A | 3/1993 | Bonutti | |
| 5,222,963 A | 6/1993 | Brinkerhoff et al. | |
| 5,224,497 A | 7/1993 | Ehlers | |
| 5,290,284 A | 3/1994 | Adair | |
| 5,303,719 A | 4/1994 | Wilk et al. | |
| 5,320,630 A | 6/1994 | Ahmed | |
| 5,342,393 A | 8/1994 | Stack | |
| 5,496,332 A | 3/1996 | Sierra et al. | |
| 5,591,177 A | 1/1997 | Lehrer | |
| 5,653,690 A | 8/1997 | Booth et al. | |
| 5,709,224 A | 1/1998 | Behl et al. | |
| 5,741,297 A | 4/1998 | Simon | |
| 5,746,692 A | 5/1998 | Bacich et al. | |
| 5,776,141 A | 7/1998 | Klein et al. | |
| 5,788,715 A | 8/1998 | Watson, Jr. et al. | |
| 5,788,716 A | 8/1998 | Kobren et al. | |
| 5,792,153 A | 8/1998 | Swain et al. | |
| 5,797,952 A | 8/1998 | Klein | |
| 5,807,236 A | 9/1998 | Bacich et al. | |
| 5,807,239 A | 9/1998 | DiBernardo | |
| 5,826,584 A | 10/1998 | Schmitt | |
| 5,843,121 A | 12/1998 | Yoon | |
| 5,846,255 A | 12/1998 | Casey | |
| 5,853,422 A | 12/1998 | Huebsch et al. | |
| 5,868,760 A | 2/1999 | McGuckin, Jr. | |
| 5,871,475 A | 2/1999 | Frassica | |
| 5,873,815 A | 2/1999 | Kerin et al. | |
| 5,885,258 A | 3/1999 | Sachdeva et al. | |
| 5,895,412 A | 4/1999 | Tucker | |
| 5,908,429 A | 6/1999 | Yoon | |
| 5,921,993 A | 7/1999 | Yoon | |
| 5,935,056 A | 8/1999 | Kerin et al. | |
| 5,935,098 A | 8/1999 | Blaisdell et al. | |
| 5,935,137 A | 8/1999 | Saadat et al. | |
| 5,954,715 A | 9/1999 | Harrington et al. | |
| 5,957,936 A | 9/1999 | Yoon et al. | |
| 5,989,580 A | 11/1999 | Wallace et al. | |
| 6,007,551 A | 12/1999 | Peifer et al. | |
| 6,019,757 A | 2/2000 | Scheldrup | |
| 6,024,756 A | 2/2000 | Huebsch et al. | |
| 6,042,590 A | 3/2000 | Sporri et al. | |
| 6,042,591 A | 3/2000 | Mears | |
| 6,059,797 A | 5/2000 | Mears | |
| 6,066,139 A | 5/2000 | Ryan et al. | |
| 6,066,147 A | 5/2000 | Mears | |
| 6,068,626 A | 5/2000 | Harrington et al. | |
| 6,074,341 A * | 6/2000 | Anderson et al. | 600/29 |
| 6,077,289 A | 6/2000 | Mollenauer | |
| 6,117,159 A | 9/2000 | Huebsch et al. | |
| 6,183,496 B1 | 2/2001 | Urbanski | |
| 6,190,353 B1 | 2/2001 | Makower et al. | |
| 6,231,561 B1 | 5/2001 | Frazier et al. | |
| 6,261,309 B1 | 7/2001 | Urbanski | |
| 6,312,446 B1 | 11/2001 | Huebsch et al. | |
| 6,355,052 B1 | 3/2002 | Neuss et al. | |
| 6,375,671 B1 | 4/2002 | Kobayashi et al. | |
| 6,461,320 B1 | 10/2002 | Yencho et al. | |
| 6,558,400 B2 | 5/2003 | Deem et al. | |
| 6,589,266 B2 * | 7/2003 | Whitcher et al. | 606/200 |
| 6,616,685 B2 | 9/2003 | Rousseau | |
| 6,623,508 B2 | 9/2003 | Shaw et al. | |
| 6,626,930 B1 | 9/2003 | Allen et al. | |
| 6,629,534 B1 | 10/2003 | St. Goar et al. | |
| 6,666,873 B1 | 12/2003 | Cassell | |
| 6,776,785 B1 | 8/2004 | Yencho et al. | |
| 6,942,674 B2 | 9/2005 | Belef et al. | |
| 6,960,224 B2 | 11/2005 | Marino et al. | |
| 7,018,388 B2 | 3/2006 | Yencho et al. | |
| 7,022,127 B2 | 4/2006 | Suyker et al. | |
| 7,108,702 B2 | 9/2006 | Yencho et al. | |
| 7,149,587 B2 | 12/2006 | Wardle et al. | |
| 7,445,623 B2 * | 11/2008 | Mialhe | 606/157 |
| 7,608,086 B2 | 10/2009 | Tanaka et al. | |
| 7,625,392 B2 | 12/2009 | Coleman et al. | |
| 7,704,268 B2 * | 4/2010 | Chanduszko | 606/213 |
| 7,803,195 B2 | 9/2010 | Levy et al. | |
| 7,833,280 B2 | 11/2010 | Stack et al. | |
| 7,846,174 B2 | 12/2010 | Baker et al. | |
| 7,892,214 B2 | 2/2011 | Kagan et al. | |
| 2002/0183768 A1 | 12/2002 | Deem et al. | |
| 2003/0158563 A1 | 8/2003 | McClellan et al. | |
| 2003/0158578 A1 | 8/2003 | Pantages et al. | |
| 2003/0171774 A1 | 9/2003 | Freudenthal et al. | |
| 2004/0116992 A1 | 6/2004 | Wardle et al. | |
| 2004/0122456 A1 | 6/2004 | Saadat et al. | |
| 2004/0243155 A1 | 12/2004 | Yencho et al. | |
| 2005/0043759 A1 | 2/2005 | Chanduszko | |
| 2005/0055050 A1 | 3/2005 | Alfaro | |
| 2005/0070935 A1 | 3/2005 | Ortiz | |
| 2005/0075665 A1 | 4/2005 | Brenzel et al. | |
| 2005/0149071 A1 | 7/2005 | Abbott et al. | |
| 2005/0251209 A1 | 11/2005 | Saadat et al. | |
| 2005/0267524 A1 | 12/2005 | Chanduszko | |
| 2005/0273124 A1 | 12/2005 | Chanduszko | |
| 2005/0277966 A1 | 12/2005 | Ewers et al. | |
| 2005/0288786 A1 | 12/2005 | Chanduszko | |
| 2006/0144406 A1 * | 7/2006 | Nikolchev et al. | 128/830 |
| 2006/0190036 A1 | 8/2006 | Wendel et al. | |
| 2006/0196137 A1 | 9/2006 | Brenzel et al. | |
| 2006/0211999 A1 | 9/2006 | Fangrow | |
| 2006/0212127 A1 | 9/2006 | Karabey et al. | |
| 2006/0217748 A1 | 9/2006 | Ortiz | |
| 2006/0265004 A1 | 11/2006 | Callaghan et al. | |
| 2007/0021758 A1 | 1/2007 | Ortiz | |
| 2007/0227544 A1 * | 10/2007 | Swann et al. | 128/831 |
| 2007/0233162 A1 | 10/2007 | Gannoe et al. | |
| 2008/0147101 A1 | 6/2008 | Ortiz et al. | |
| 2010/0004681 A1 | 1/2010 | Coleman et al. | |

FOREIGN PATENT DOCUMENTS

| | | |
|---|---|---|
| WO | WO-0009040 A1 | 2/2000 |
| WO | WO-0149185 A1 | 7/2001 |
| WO | WO-0205718 A2 | 1/2002 |
| WO | WO-03034927 A1 | 5/2003 |
| WO | WO-2007013070 A1 | 2/2007 |
| WO | WO-2007073566 A1 | 6/2007 |
| WO | WO-2008008178 A2 | 1/2008 |
| WO | WO-2008040577 A1 | 4/2008 |

* cited by examiner

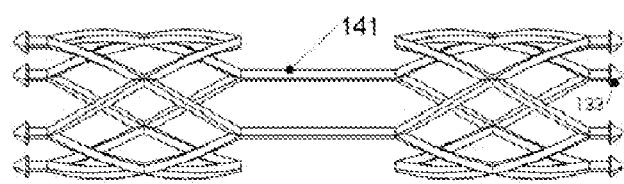
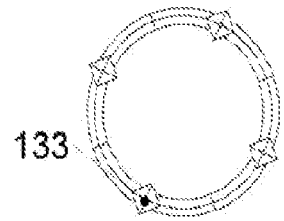
Figure 22A
Figure 22D
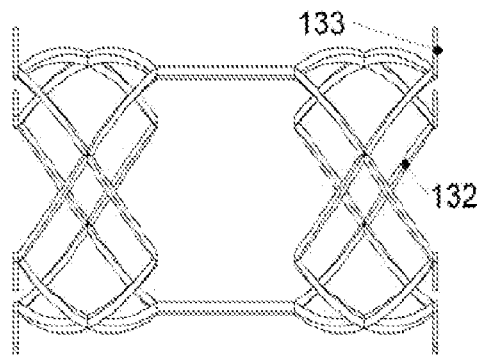
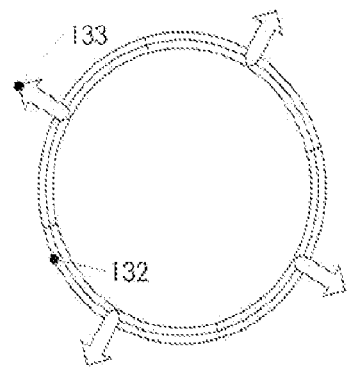
Figure 22B
Figure 22E
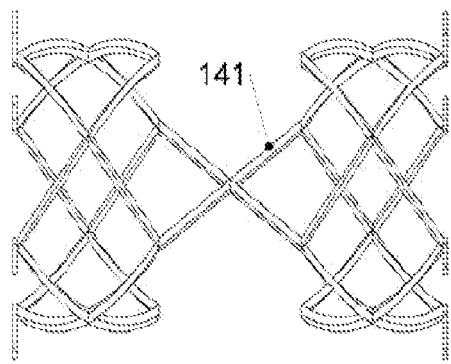
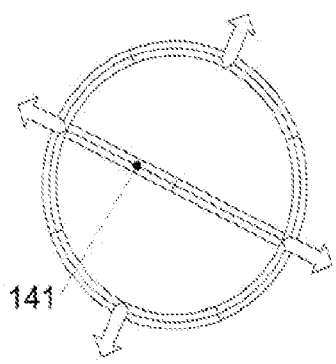
Figure 22C
Figure 22F

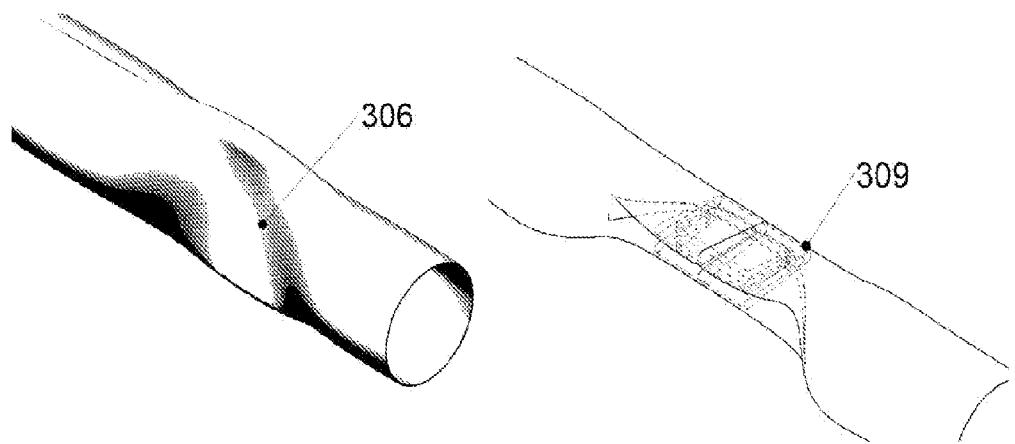
Figure 38A                                     Figure 38B
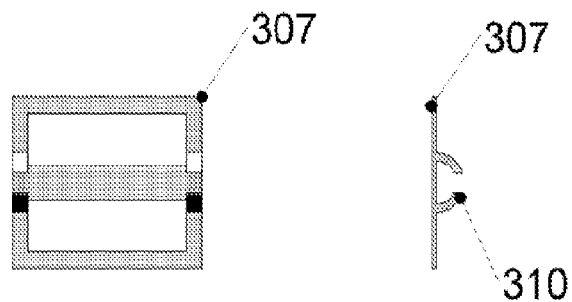
Figure 38C                                     Figure 38D
Figure 38E                                     Figure 38F

METHODS AND APPARATUS FOR OCCLUSION OF BODY LUMENS

RELATED APPLICATIONS

This application claims priority to International Patent Application No. PCT/US2008/057357, International Filing Date 18 Mar. 2008, entitled Methods And Apparatus For Tubal Occlusion, which claims priority to U.S. Provisional Application Ser. No. 60/895,707 filed Mar. 19, 2007 entitled Methods And Apparatus For Tubal Occlusion, both of which are hereby incorporated by reference.

BACKGROUND OF THE INVENTION

There are many clinical problems or needs which may be treated through procedures to create permanent occlusion of body lumens. Some examples of these are the occlusion of fallopian tubes to sterilize a female patient, occlusion of the vasa deferentia for sterilization of a male patient, the occlusion of varicose veins, occlusion of arteries feeding regions of cancerous tumors, occlusion of the bile ducts, or the occlusion of arteries in the neuro-vasculature to isolate aneurysms.

In the case of female sterilization, there are many different approaches by which this procedure can be performed. These include: full surgical procedures, small incision surgical procedures, and trans-cervical approaches. The specific method of creating the occlusion can also vary. In surgical approaches, the fallopian tubes can be occluded by applying a clip or suture to pinch the tubes closed or by using energy application to seal the tubes closed. These approaches tend to be acutely effective but also require the invasiveness and consequent recovery of surgical procedures.

In trans-cervical approaches for female sterilization, multiple technologies have been developed in the last 10-15 years which utilize implants in the fallopian tubes delivered through scopes and catheters via the cervix and uterus. These implants act in different ways including energy delivery, inflammatory materials to provoke a healing response, and physical plugging. An example of a plugging approach is shown in U.S. Pat. No. 3,805,767. Pure mechanical plugging approaches have not been well accepted to date due to a relatively high rate of ejection of the plugs by the body. Other implants have relied upon a proliferative response of the body to the implant. These techniques may rely on this body response to both anchor the implant permanently and to complete the occlusion of the fallopian tube. Examples of this approach are described in a family of patents to Nikolchev et al. including U.S. Pat. Nos. 6,176,240, 6,634,361, 6,679,266, 6,684,884 and 6,705,323. U.S. Pat. No. 7,073,504 also discloses an approach for use in either the fallopian tubes or the vasa deferentia for implanting a device having an open structure which enables tissue ingrowth to complete the occlusion of the lumen.

All of the trans-cervical technologies which have been introduced to date which have shown good enough effectiveness and reliability to achieve common use have had a common limitation. This is that they require a healing response to the implant to yield a reliable occlusion of the fallopian tube. Consequently they also often require follow up assessment after some period of time to allow the healing response to progress to a degree to assure that the procedure has been effective. This can present reliability issues because it requires the patient to use another form of birth control in the interim period before the occlusion has been verified. It also is inconvenient for the patient and more expensive with the need for the follow up assessment.

U.S. Pat. No. 6,896,682 does disclose an apparatus which is intended to create an acute occlusion with the application of an o-ring over an inverted segment of the fallopian tube via a transcervical approach. This approach is still clinically unproven at this time.

For these reasons and others there is a need for a new method and apparatus which enables reliable occlusion of body lumens through a non-surgical approach which is both effective more quickly or acutely and is permanent.

OBJECTS AND SUMMARY OF THE INVENTION

The present invention provides methods and apparatus for creating occlusion of the fallopian tube or other body lumen. The devices are most often permanent implants which facilitate an acute occlusion of the desired body lumen via a non-surgical approach using catheters and/or scopes to access the site of desired lumen occlusion. All of the methods and apparatus of the current invention act to bring the tissue of the lumen wall into contact or close proximity with the adjacent tissue and tissue of the opposing wall to help create an acute occlusion or significant reduction in the lumen opening to help facilitate a faster permanent occlusion of the lumen. These methods and apparatus manipulate the tissue by twisting, plicating, bunching, flattening, tensioning, folding, plugging, axial rotation, rotation perpendicular to the axis, folding perpendicular to the axis, folding axially, folding radially, stretching or tensioning axially, stretching or tensioning perpendicular to the axis, compression axially, compression perpendicular to the axis, compression radially, inverting axially, inverting perpendicular to the axis, and any combinations of these actions resulting in the desired effect of occluding, or closing a tissue lumen. For purposes of illustrating the method and devices, the invention will be described as it could be used to create occlusion of the fallopian tubes. It is intended that these same techniques can also be effective for other anatomies such as those described earlier.

For all but one embodiments described, the common approach is to create an acute blockage or significant reduction in lumen opening and to rely on the healing together of the tissue surfaces to make this blockage permanent so that the action of the implant is no longer important. This healing together of the tissue can be aided by an injury to or irritation of the tissue to trigger a healing response. This allows for the use of a variety of materials for the components of the implants to: address requirements of the acute function of the device, avoid long term issues of galvanic corrosion or stored energy, augment the acute seal with spermicidal/ovacidal materials, use materials which accelerate the healing response, facilitate energy delivery through the implant, or use biodegradable materials for some or all components of the implant.

It is anticipated that the devices and methods described may not yield an absolute blockage acutely, but still bring the tissue into contact over the inner surfaces of the lumen wall. This scenario can still be a significant improvement over the existing art as the time required for the healing response to create a reliable absolute blockage of the tube should be on the order of a few weeks with the tissue in close proximity as opposed to current methods which require months of healing response for the desired outcome.

BRIEF DESCRIPTION OF THE DRAWINGS

FIGS. 22A-22F show a sequence of deployment for an embodiment of the invention having expandable anchor members and connecting elements between the anchors members which twist.

FIGS. 38A-38F show another embodiment of a device which flattens and folds the lumen along its axis when implanted.

DETAILED DESCRIPTION OF THE INVENTION

A first embodiment of the device of the invention uses twisting of a segment of the body lumen as a primary mechanism to create the blockage of the lumen. A device of this embodiment has a distal anchor component which is introduced in a reduced diameter state into the lumen to be occluded.

The distal anchor component is then expanded up to engage the tissue of the tube wall. The expansion of this distal anchor element can be the result of elastic recoil towards its natural unconstrained size. This, and all of the following described systems, can anchor to the tissue either passively (via friction) or actively (via barbs or other adhering means). This anchor component can be a self expanding stent type structure made from a material such as nitinol. This anchor component can have a round cross section like most conventional stent structures. It also can be a flat structure so that it flattens the lumen when it is expanded inside it. This flat structure embodiment can be cut from a flat sheet of nitinol using techniques similar to those used to cut stents from round metal tubes.

After expansion, this component can be torqued relative to the tissue lumen by torquing the delivery system. This acts to twist the lumen creating the desired twisted blockage in the lumen over the central shaft coupling the distal anchor element back to the proximal anchor element (still inside the delivery system).

Next the proximal anchor component is advanced out of the delivery system and expands up to engage the wall of the lumen proximal to the twist in the lumen which was created with the earlier torquing action. This proximal anchor element can engage the tissue wall in one of the same ways described earlier for the distal anchor. This acts to fix the proximal anchor element to the tissue wall and maintain the twist in the body lumen between the two anchor elements. By engaging the anchor elements to the tissue wall on either side of the twist in the lumen, the device acts to retain the acute closure of the lumen created by the twist. The implant is then decoupled from the delivery system leaving the implant behind and the lumen blocked. The coupling of the implant to the delivery system can be a threaded connection or a pinned connection to name two simple and well known possible releasable coupling methods. The central shaft in this embodiment preferably has a very small cross section and is solid for at least a portion of its length through the region of twisted down tissue so that it can't act as a path for sperm to pass through the blockage in the lumen. The amount of twist needed to be imparted to the tissue to achieve either a complete occlusion of the lumen or at least occlusion of the vast majority of the lumens cross section may be between 45 degrees and 360 degrees of rotation.

Figure 1:
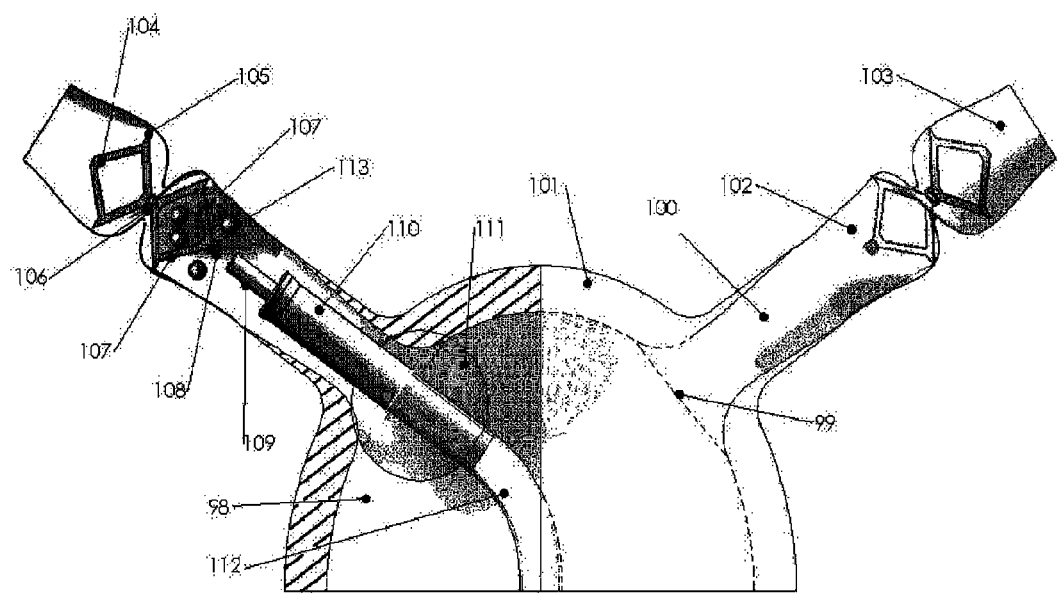
FIG. 1 is a simplified cross-sectional view of a patient's Uterus and Fallopian Tubes, showing illustrative tubal occlusion in accordance with the invention.

FIG. 1 shows a uterus 101 and occluded fallopian tubes 100 in accordance with a first illustrative embodiment of the invention. The structures shown in FIG. 1 are the uterus 101 and typically occurring fallopian tubes 100. The fallopian tubes 100 communicate with the uterus 101 in a single planar orientation, but may also have a multi-planar orientation. The fallopian tubes 100 allow passage of eggs proximally from tubal section 103 towards tubal section 102 and into the uterus 101. Conversely fallopian tubes 100 can allow passage of sperm or other media to pass distally from tubal section 102 towards distal tubal section 103. For simplicity in the present discussion, it will generally be assumed that distal refers to the ovarian direction of the fallopian tube 100, not shown here, and proximally refers to the tubal ostium 99 direction of the fallopian tubes 100.

FIG. 1 illustrates a simplified view of the uterus, fallopian tubes and surrounding anatomy. FIG. 1 is intended to illustrate the first embodiment of the occlusion of the fallopian tubes 100. It should be noted that the fallopian tubes are desired to be closed from time to time to prevent pregnancy, and for other clinical reasons understood. The typical surgical procedure involves clipping, banding, suturing, RF energy, etc. in the region described between 102 and 103. It should also be noted that surgical occlusion can be accomplished in any region from the tubal ostium 99, distally to the ovaries, not shown here. The typical surgical procedure utilizes 1-5 cm to occlude the fallopian tube 100. It should be noted that the embodiment described in FIG. 1, will utilize a similar magnitude of tubal length, but is not limited to this effected length or location. The above mentioned typical surgical procedure requires surgical incisions to access the external portion of the fallopian tubes 100 to apply the clip, suture, RF, etc.

FIG. 1 shows a first illustrative embodiment of treatment of the fallopian tubes in accordance with the invention. The illustrative treatment embodiment includes cannulating the fallopian tube 100 with delivery sheath 110 up to delivery positioning mechanism 111. The treatment being described further includes the deployment and engagement of the distal fallopian tube 100, by the distal anchor element 104. The treatment further includes the delivery apparatus 109, which imparts a torsional or twisting force on the fallopian tube 100. The proximal anchor element 107 is subsequently deployed, effectively locking the twisted tubal section in place. The release mechanism 108 is then decoupled from the implant structure. The treatment may further include a diagnostic evaluation utilizing bubbles 113 or suitable diagnostic media. Media 113 should not pass from proximal fallopian tube lumen 102 to distal fallopian tube lumen 103, or the implant can be re-deployed or removed.

FIG. 1 shows the first illustrative embodiment of the invention, to achieve transcervical tubal ligation. Transcervical tubal ligation involves the introduction of certain instruments through the cervical opening to access the uterus chamber 98. Upon introduction into the uterus chamber 98, the physician or operator, can visualize and access the fallopian tubes 100, through the fallopian tube ostium 99. A typical instrument, but only one possible technique, is the hysteroscope used to cross the cervix through the vaginal opening and access the tubal ostium 101a. The hysteroscope, not shown here, has both visualization and working instrument channel capability. It is understood that the invention described in FIG. 1 and all subsequent methods and apparatus in the specification will be compatible with typical and specialty transcervical tools. The first embodiment, FIG. 1 illustrates a delivery sheath 110 that fits through and works with the hysteroscope described above. All aspects of the embodiment shown in FIG. 1 fit through the hysteroscope, function in conjunction with typical hysteroscopic procedures; allow visualization during the procedure, and all other aspects of necessary functionality.

Another advantage of the embodiments illustrated in FIG. 1 is the acute nature of the occlusion of the fallopian tube 101. The relative torsional motion between distal anchor element 104 and proximal anchor element 107 creates acute occlusion. Acute occlusion is intended to be immediate up to 14 days post implant, which allows for further ingrowth of healing cells and tissues. Healing tissues ingrowth may or may not need to occur anywhere within the fallopian tube 100 region of the implant to facilitate complete occlusion. Relative torsion motion, described above, is intended to indicate between 45 and 360 degree's of both implant and connected tissue motion. It is presented that distal anchor structure 104 is expanded to engage and anchor to the corresponding distal fallopian tube section. Thus, rotational movement of distal anchor structure 104 creates a resulting fallopian tube wall rotational motion.

Proximal anchor structure 107 will have similar fallopian tube wall anchoring capability. It should be noted that the mechanical properties and interface of the hysteroscope, delivery sheath 110, positioning mechanism 111, with the fallopian tube ostium 101a will create suitable stabilization or reactionary forces for rotational movement of distal anchor structure 104 and the corresponding section of fallopian tube 100. Also, the proximal anchor structure 107 will interface with the corresponding fallopian tube section to create a mating force suitable to lock the relative twisting in place. To be clear, distal anchor 104 will be moved rotationally causing the adjoined fallopian lumen and wall to move and rotate correspondingly. The delivery sheath 110 delivery positioning mechanism 111, in combination with the hysteroscope instrumentation, will be fixed relative to the motion of anchor 104. Once the desired twist of the fallopian tube 100 is achieved, proximal anchor 107 will be deployed and engage rigidly to the fallopian tube 100 lumen and wall thickness, effectively locking the net twist and occlusion of the fallopian tube in place.

In another embodiment of this invention it is possible to use the distal and proximal anchor elements as two poles or electrodes to apply a bi-polar energy between the anchors to induce a localized healing response in the twisted tissue between the anchor elements. This may have the benefit of shortening the time during which the occlusion of the lumen is dependant upon the mechanical action of the implant by having the healing response create a permanent tissue occlusion more quickly. Multiple energy forms are possible for this embodiment including radio frequency, ultrasonic, microwave or others known in the art.

In another embodiment of this invention materials such as copper, polyester, sclerosing agents or other irritant materials or drugs/medications may be incorporated with the structures of the anchor elements, the central shaft or both to induce inflammation and a healing response to create a permanent tissue occlusion no longer dependant upon the mechanical action of the implant.

The following is one possible sequence of steps for implantation of devices of some of the described embodiments in the fallopian tubes of a female patient.
1. Pre-Procedure Narcotics Taken—Relax Patient and Aid in Cervical Dilation
2. Cervical Block Given—Kits are available including local anesthetic
3. Hysteroscopy used for uterus access
4. Position sheath across cervix
5. Position scope in uterus
6. Inflate and visualize both ostia of the fallopian tubes
7. Focus scope on left or right ostium
8. Delivery device tracks into targeted fallopian tube
9. Delivery device inserted up to mark at ostium
10. Distal Anchor Deployed
11. Tube Twisted Closed by torsion applied through delivery device to distal anchor
12. Proximal anchor deployed locking twist in tissue of fallopian tube
13. Verify acute closure through imaging via hysteroscopy, ultrasound or other
14. If not closed—remove or redeploy
15. Decouple implant from delivery system
16. Repeat for Second fallopian tube.

This is only one possible scenario of a delivery sequence for one specific anatomy and is given to be illustrative of how a procedure could go with some of the described embodiments. Other embodiments described might have variations on this sequence as appropriate for their differences in actuation or design. This sequence might also vary for procedures in other anatomies.

FIG. 1 shows a first illustrative embodiment which includes an implant apparatus intended to engage and twist the fallopian tube structure. The distal anchor structure 104 and proximal anchor structure 107 are both intended to initially be introduced through the delivery sheath 110, in a mostly constrained or compressed state. Once positioned appropriately in fallopian tube 100, the anchors will substantially change shape, elastically, or plastically or both, to properly engage the fallopian tube 100. The engagement of the fallopian tube 100 by anchors 104 and 107 can be accomplished with radial pressure by anchor members, penetrating features such as anchor barb 105, or combinations thereof. It is understood that anchor barb 105, and related apparatus described later in this specification may engage without piercing luminal tissue, may partially pierce through the fallopian tube 100 wall, or pierce entirely through the fallopian tube 100 wall. It is also described that the amount of radial pressure can be tailored for each anchor mechanism to provide adequate anchoring pressure and interlocking forces between the anchor and tube to create the described torsion forces, and other force directions described later, without producing an unacceptable amount of physiologic trauma.

Another Advantage of the embodiments illustrated in FIG. 1 is the reversible, removable, and re-deployable nature of this approach. Both anchor 104 and anchor 107, are capable of being re-constrained back into the delivery sheath by reversing the deployment steps. Once in the sheath, the operator will have the option of repositioning the sheath and subsequent anchor deployments, or remove the entire system.

In another embodiment of this invention it is anticipated that it would be possible to assess the completeness of acute occlusion achieved after deployment of the proximal anchor element and prior to decoupling the implant from the delivery system. This assessment could be done visually using a small optical scope passed through or included in the delivery sheath. A technique such as this would allow the deployment to be assessed before release of the implant and therefore the deployment could be reversed or modified if the result was not as desired. Yet another advantage of the illustrative embodiment is the technique for confirming acute closure of the fallopian tube 100. Echopaque or Radiopaque media can be injected or distributed into the implant site. Subsequently the user can utilize certain imaging techniques, such as hand-held ultrasound or portable fluoroscopic equipment, to confirm that the lumen has been properly occluded. It should be noted that this methodology could be utilized before and/or after the initiation of the occluding implant procedure. The distal tubal lumen 103 can be pre-filled with certain media described above, or rely on air or naturally occurring media that already exists in fallopian tube lumen 103. Once introduction into fallopian tube lumen 102 occurs, the absence or presence of certain media relative to 103 can be ascertained. The appropriate clinical judgment can then be made, to either proceed with the procedure or discontinue the procedure. Confirmation of acute closure may also be checked with visual inspection using a small scope introduced into the fallopian tube with the delivery sheath for imaging. Confirmation of closure may also be assessed with other advanced imaging techniques such as CT, MRI, and Electromagnetic, pressure decay, and other types of imaging and various sensors.

It should also be mentioned that the apparatus will be constructed out of typical medical device materials including but not limited to materials currently used in medical devices such as nitinol, stainless steel, copper, metals, polymers, plastics, tissue, collagen, alloys, composites and other materials commonly used in the practice.

It should also be mentioned that the device can be made out of materials and will be located in such a place that the implant will be compatible with other women's health procedures such as RF energy application for menorrhagia. This can be done through material selection or by locating the device so that no metal is in proximity to the uterus in the device as implanted. Materials used can also be optimized for MRI compatibility.

It should also be noted that a relatively short length of fallopian tube 100 can be utilized for this procedure. This aspect is important because of the potential need to reverse the tubal occlusion procedure. A surgical procedure, involving the cutting and reattachment of fallopian tube using end-to-end anastomosis, is the typical method of reversing a ligation procedure. The illustrative invention shown in FIG. 1 and throughout this specification is intended to use a length of fallopian tube that will also allow reversal procedures to be done.

Figure 2:
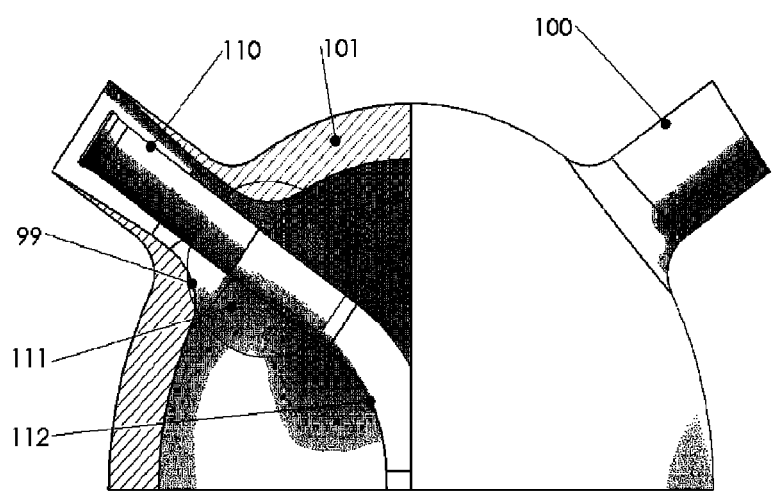
FIG. 2 represents the first step of the procedural sequence represented in FIG. 1, Cannulation of the Fallopian Tube ostium.

Illustrative methods and instrumentation for transcervical occlusion and apparatus for twisting tubes down to a substantially closed state as shown in FIG. 1 is shown in FIG. 2 et seq. FIG. 2 shows the first step of the transcervical tubal occlusion procedure. A delivery sheath 110 is introduced into the fallopian tube 100. It should be noted that the transcervical placement of certain equipment such as a hysteroscopy will have already been complete. It should also be noted that the inventions described in this specification will be compatible with all necessary equipment to access and work within the uterus cavity. Typically the hysteroscopes have a working lumen in which devices are passed to perform procedures. The working lumen may be 5.4 Fr in diameter in commonly used models. It may also be larger or smaller. Hysteroscopes may also be straight, rigid, and have forward or angled viewing lenses at the end. The described delivery sheath 110 and associated embodiments are intended to be compatible with both rigid and flexible scopes. It should also be noted that the scope could be included in the delivery device itself. The hysteroscopes also typically contains a lumen for irrigation and aspiration during the procedure.

The illustrative embodiment shown in FIG. 2 depicts a delivery sheath 110 engaged in the fallopian tube 100. The delivery sheath 110 is intended to be flexible enough to properly transition from the hysteroscope into the fallopian tube 100. Variation in both the uterus 101 and the fallopian tube 100 and the geometrical relation between these two are anticipated in the construction of the delivery sheath 110. The flexibility, tip length, column strength, kink resistance, and atraumatic tip, are intended to accommodate the anatomy and facilitate delivery of the devices intended to occlude the fallopian tube 100. The delivery sheath proximal 112 depicts a curve and the associated distal tip length described above.

The delivery positioning mechanism 111 shown in FIG. 2 is shown as an expandable balloon-like structure which acts as a physical stop for the delivery sheath 110. The delivery positioning mechanism can also serve to create a seal against the tubal ostium 99. This secondary attribute allows for the irrigation or aspiration of the fallopian tube 100, through the hysteroscope working channel or from another source. The injected media, such as a radiopaque or echopaque substance, will preferentially stay in the fallopian tube 100. Also, an elevated pressure can be achieved before and/or after the fallopian tube 100 has been occluded. For instance, proximal fallopian tube lumen 102 can be at a higher pressure and containing certain diagnostic media than the distal fallopian tube lumen 103. The physician or technician can than ascertain that the tube is suitably closed and the implant can then be released from the delivery apparatus 109. Conversely, passage of the diagnostic media from lumen 102 to lumen 103, under certain parameters after the fallopian tube 100 has be occluded would indicate that the device should be removed and either redeployed or the procedure discontinued.

Figure 3:
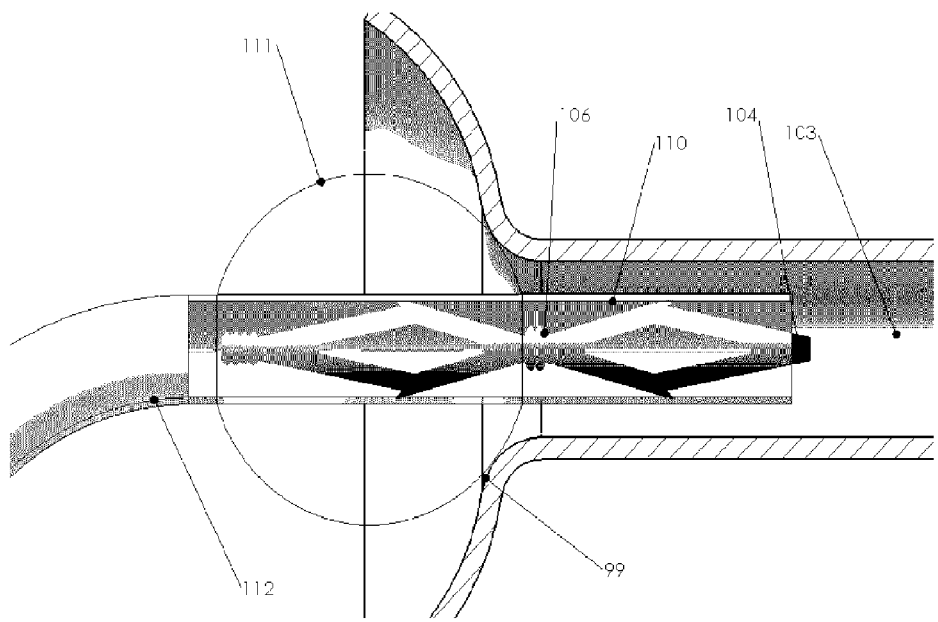
FIG. 3 is still another stage in the procedure represented in FIG. 1 in which the distal anchor extends from the delivery sheath.
Figure 4:
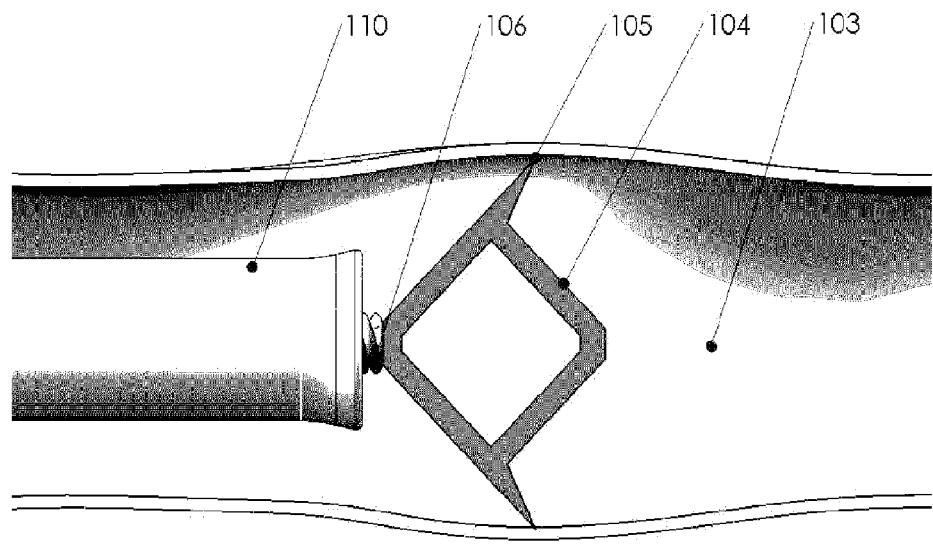
FIG. 4 is an enlarged cross-sectional representation of the next treatment stage represented in FIG. 3 in which the distal anchor expands to engage Fallopian Tube wall.

The next aspect of the illustrative invention being presented is shown in FIG. 3 and FIG. 4, anchor 104 has been advanced out of the delivery sheath 110. The distal anchor 104 is being described as a self-expanding structure, capable of being constrained with in the delivery sheath 110. Upon advancement distally, the distal anchor element expands in the radial orientation, engaging the distal fallopian tube lumen. Those skilled in the art understand the basic design requirements for a cellular self-expanding flat or multi-planar structure. Material selection, material processing, strut and joint design requirements are anticipated. The wall of the fallopian tube 100 is engaged by both radial pressure exerted from the distal anchor element and the anchor barb 105. It should be noted that both radial pressure and the barb element can be tailored to properly anchor the structure to the wall. It should also be noted that the basic distal anchor element presented will later be described in alternative forms. The first illustrative embodiment is intended to describe the key elements and overall procedural methodology.

Figure 5:
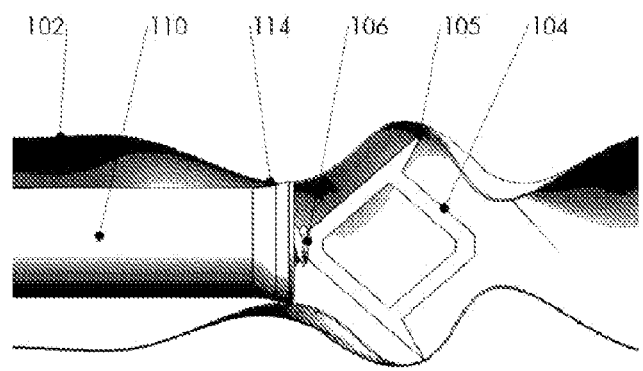
FIG. 5 is another treatment stage in accordance with the invention in which the distal anchor expands and the center implant portion exerts torsion on the tubal structure.

The next aspect of the illustrative invention being presented is shown in FIG. 5. FIG. 5 depicts the distal anchor element 104 engaged with the distal fallopian tube lumen 103 in such a way as to effect rotational movement of the entire luminal wall of the fallopian tube 100. After the distal anchor element 104 is suitably engaged with the wall, the user will actuate a control mechanism in a handle of the delivery device 109. This control mechanism will allow the user to selectively twist the fallopian tube into a closed or mostly occluded state. The user will actuate rotational movement through the member attached to implant and transmit rotational energy through a rigid implant center section 106. The user can apply between 45 and 360 degrees of rotation. The user can then selectively test the closure of the fallopian tube 100 with the diagnostic tests described earlier or move to the next procedural step. If the user is not satisfied with the result of this torsion step, the distal anchor element 104 can be rotated back to its original state and then be retracted into the delivery sheath 110. The user can then choose to reposition the delivery sheath 110 and redeploy the device or remove the entire assembly from the body.

Figure 6:
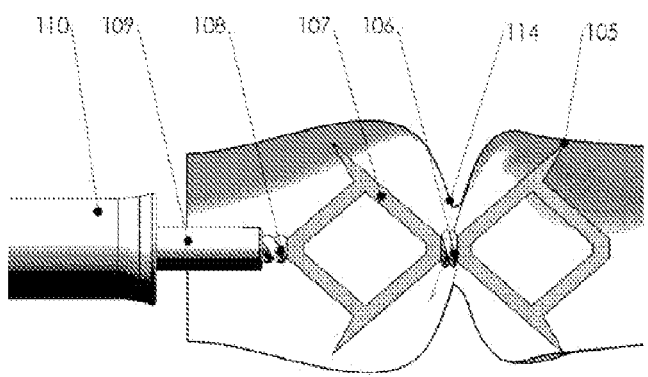
FIG. 6 is yet another stage of the treatment in accordance with the invention in which the proximal anchor deploys with a locking torsional effect.

The next aspect of the illustrative invention being presented is shown in FIG. 6. FIG. 6 shows the proximal anchor element 107 deployed in the proximal fallopian tube lumen 102. FIG. 6 also show the delivery apparatus 109 which is connected to the proximal anchor element 107 by the anchor/delivery release mechanism 108. It is shown that the user has twisted the fallopian tube 100 into an occluded state 114 and the proximal anchor element 107 has been deployed to lock the torsion effect in place. The net twist imparted by the user through the delivery apparatus is held in place by the two anchors and the rigid center section 106. If the user is satisfied with the result, the proximal anchor element 107 can be released from the delivery apparatus 109 by decoupling at the anchor/delivery release mechanism 108. This release mechanism is shown as a rotational screw type release mechanism. Those skilled in the art can easily anticipate multiple possible coupling configurations that would allow this delivery including but not limited to pins through keyholes, movable jaws, snap fits, screws rotational opposite of implant rotation and any other coupling linkage or mechanism commonly used in the practice.

Figure 7:
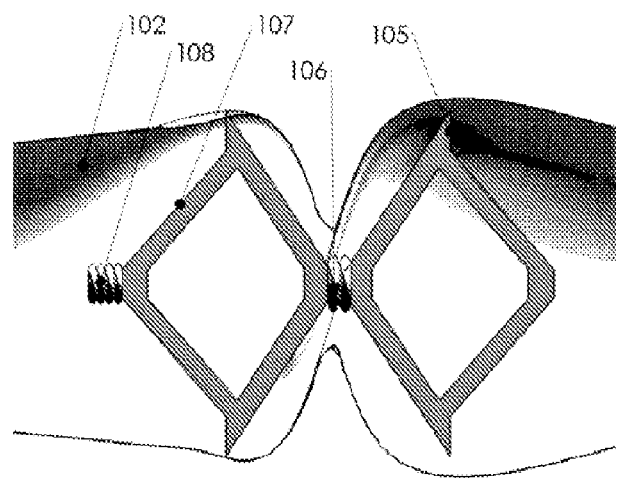
FIG. 7 is yet another stage of the treatment in accordance with the invention in which the implant and resulting occluded tubal segment release from the delivery device.

The next aspect of the illustrative invention being presented is shown in FIG. 7. The occlusion or ligation of the fallopian tube 107 is complete and the delivery apparatus 109 and associated delivery sheath 110 have been removed. It should be noted that the user could still come back at some point in the future, reattach to the implant, and recapture the entire implant, and remove the system, returning the fallopian tube to its initial state.

Figure 8:
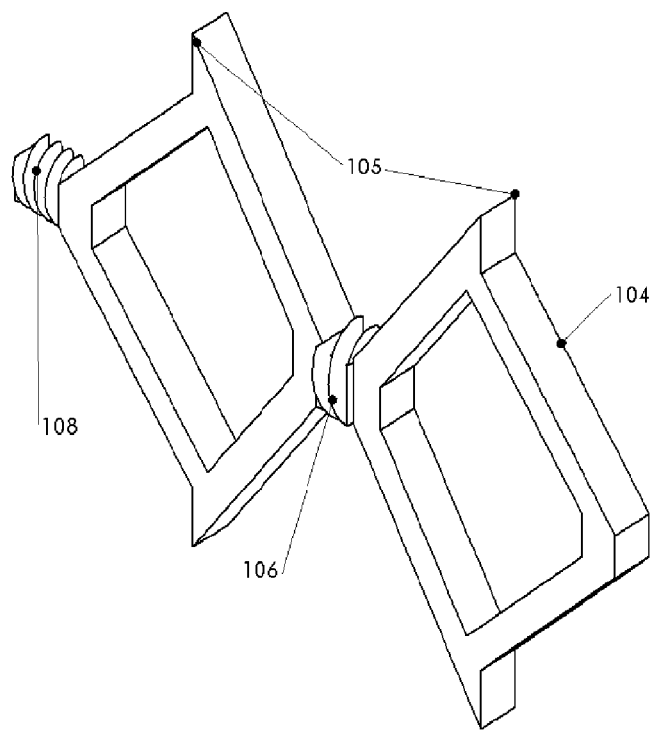
FIG. 8 is a three dimensional representation of the implant described in FIGS. 3-7.

It should be noted that the above delivery procedure can be modified by a torsion spring as part of the implant being present instead of a rigid center section 106 as depicted in FIG. 8. This spring mechanism would allow the distal anchor 104 and proximal anchor 107 to be deployed independent of the user applying rotational movement through the delivery device. The delivery device would contain a feature that constrains the rotational spring until the user is satisfied that the anchor elements are properly deployed and that the desired twisting of the fallopian tube 100 has been achieved The spring mechanism in the 106 region would then be released causing the tube to twist.

Figure 9:
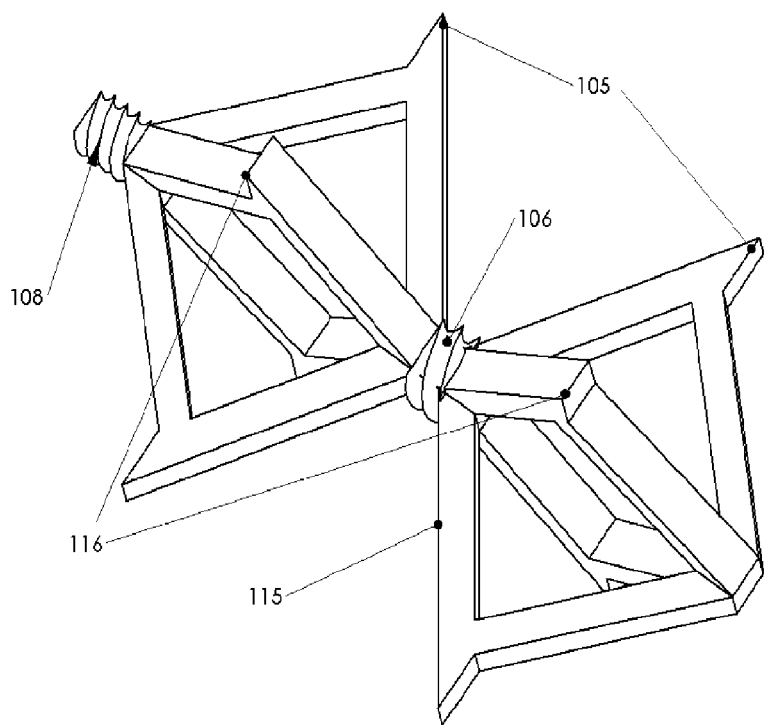
FIG. 9 is a three dimensional representation of an implant like that in FIG. 8 but having the proximal and distal elements expand as three dimensional structures.

FIG. 9 represents another embodiment of the anchoring elements. This depicts a multi-planar anchoring structure capable of achieving the above mentioned procedures. FIG. 9 could be constructed from two distinct stent cell type structures which are then joined or a single unitary structure that creates the multi-planar anchor element 115. Also, as with FIG. 8 the center section 106 can be a torsional spring type mechanism capable of storing and transmitting rotational forces to the surrounding anchors and tissue. Multi-Planar anchor element barbs 116 are similar in construction and function to anchor barbs 105 described earlier.

Figure 10:
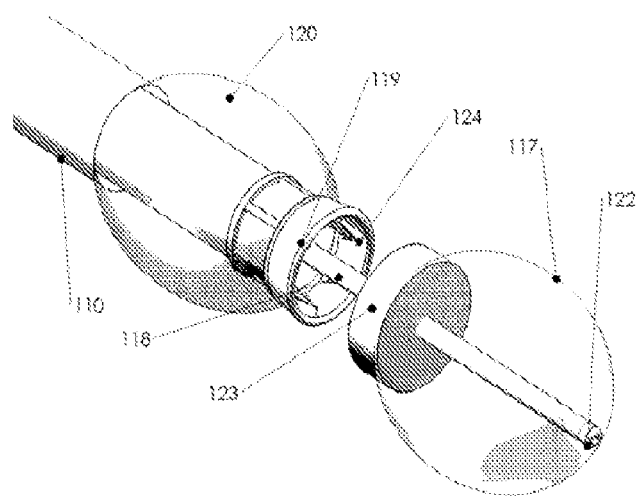
FIG. 10 shows a first step in the delivery sequence for an embodiment which twists the lumen and pierces the twisted tissue between the two ends of the implant to lock in the twist of the lumen.

An alternative or additional embodiment is shown in FIG. 10. This embodiment, as previously described in an earlier embodiment, creates a relative torsion force on the fallopian tube as a means of occlusion. Distal tip 122 is the leading edge of the embodiment and is constructed in such a way to facilitate unencumbered access within the tube while preventing unnecessary trauma to the vessel wall. Distal radially expanding device here depicted as a balloon anchor 117 is connected to central member 118. Distal balloon anchor 117 is intended to engage a fallopian tube 100 luminal segment and provide temporary anchoring. Central member 118 is attached to distal member 117 and comprises both an inflation lumen and structural element that controls rotary forces. Delivery tube 119 surrounds central member 118 and contains the distal piercing anchor element 123 and the proximal anchor element 124. Mounted on the delivery tube is proximal balloon anchor 120. Proximal radially expanding device here depicted as a balloon anchor 120 is inflated and controlled both axially and rotationally through delivery tube 119. Proximal anchor 120, like distal anchor 117, is intended to engage a fallopian tube 100 luminal segment and provide temporary anchoring. During delivery of the piercing implant 124, distal anchoring balloon 117, and proximal anchoring balloon 120 will engage the fallopian tube 100 wall and create a relative twist to the desired amount of rotation. Once the fallopian tube 100 is twisted shut, the proximal piercing anchor 124 and distal piercing anchor 123 are implanted through the manipulated tissue. The distal balloon 117 and proximal balloon 120 are then unexpanded in this case deflated and removed. Twisted fallopian tube 125 is then held in the manipulated state, thus creating an occluded lumen. The distal expanding anchor 117 and proximal expanding anchor 120 can be constructed from any known expanding structure such as those described in this entire invention and or any commonly know in the art. The delivery device described here with twisting can also be configured to exert forces that facilitate any of the desired tissue manipulation movements including but not limited to axial rotation, rotation perpendicular to the axis, folding perpendicular to the axis, folding axially, folding radially, stretching or tensioning axially, stretching or tensioning perpendicular to the axis, compression axially, compression perpendicular to the axis, compression radially, inverting axially, inverting perpendicular to the axis, and any and all combinations of these actions resulting in the desired effect of occluding, or closing a tissue lumen.

Figure 11:
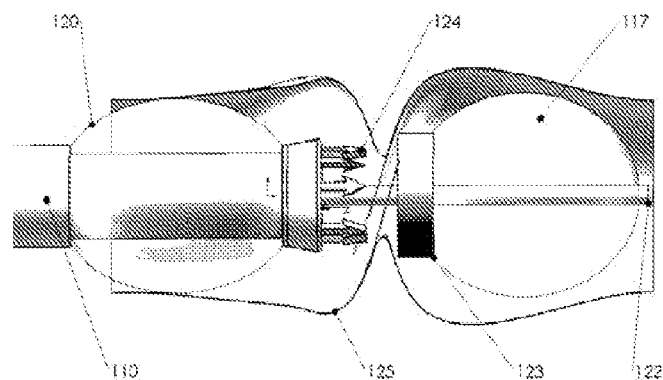
FIG. 11 is a next step in this sequence of delivery.
Figure 12:
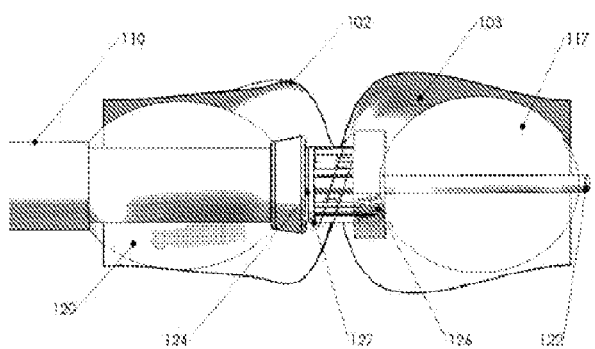
FIG. 12 is a next step in this sequence of delivery.

FIG. 11 and FIG. 12 are additional illustrations of the FIG. 10 embodiment. FIG. 12 shows in more detail the piercing member 126 and the piercing structure 127. The piercing member is shown in this embodiment in a configuration to retain tissue in a reduced configuration once pierced. It should be noted in this embodiment and all others in this specification that the piercing member(s) can also be needle shaped, have negative tapers, hooked, curved, spiral, any shape that facilitates the desired effect of tissue engagement. The piercing structure 127 is shown in a fixed diameter configuration. This structure is designed to be compatible with all the relative diameters of the procedural and delivery equipment. It should be noted that expandable versions of this piercing structure 127 will be noted later in this specification.

Figure 13:
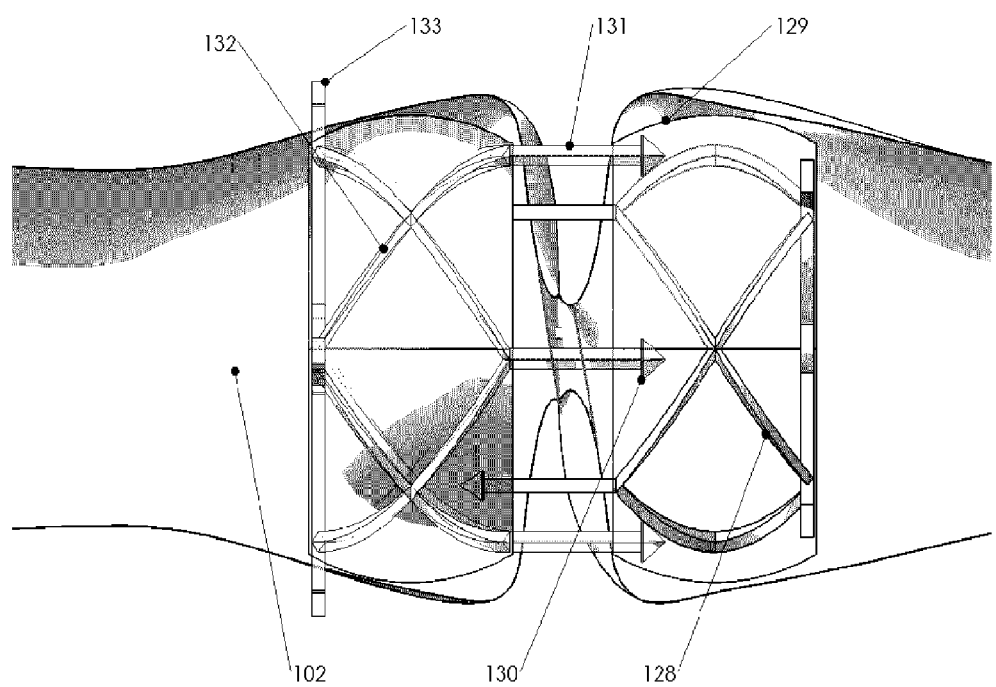
FIG. 13 is another version of an implant for the sequence described in FIGS. 10-12. This version has expandable proximal and distal elements.
Figure 14:
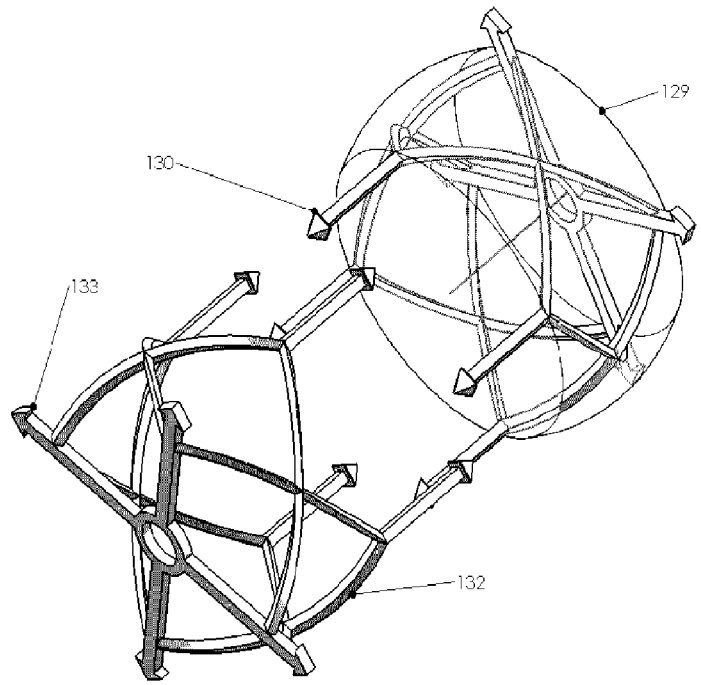
FIG. 14 is another version of an implant for the sequence shown in FIGS. 10-12. This version includes a covering over one of the expandable elements.

FIG. 13 and FIG. 14 are additional or alternative embodiments to achieve the closure of fallopian tube 100 as described in FIGS. 10, 11 and 12. The fallopian tube 100 is twisted into a substantially closed position. Embodiments depicted in FIGS. 13 and 14 work to keep the fallopian tube 100 in a substantially closed state. FIGS. 13 and 14 are expandable structures that can be introduced into the fallopian tube 100 in a reduced diameter state, then be expanded and pierce the already reduced and twisted tissue. The distal expanding piercing anchor 128 is shown in FIG. 13 along with the proximal expanding anchor 132. This is an embodiment that readily expands from a constrained state to an expanded state. To facilitate or prevent ingrowth a covering can be added to the structure. Expandable anchor covering 129 is composed of any flexible yet implantable material that will facilitate the desired design feature such as but not limited to; Dacron, PTFE, Biologics, collagen, silicon, urethanes, etc. The expandable covering 129 can be present on one or both of the fallopian tube anchors. Also shown is piercing member 131 and piercing member tip 130. Piercing member tip 131 is intended to provide the appropriate column strength for piercing while minimizing trauma and any unwanted channels in the pierced tissue. Piercing member(s) tip 130 can also be needle shaped, have negative tapers, hooked, curved, spiral, any shape that facilitates the desired effect of tissue engagement. Anchor barb 133 as illustrated earlier is intended to engage the lumen wall. It is understood that anchor barb 105, and related apparatus may engage without piercing luminal tissue, may partially pierce through the fallopian tube 100 wall, or pierce entirely through the fallopian tube 100 wall. The piercing members can also be designed to engage the opposing anchor member. The distal and proximal anchors can be designed to couple or mate together and therefore lock and engage the tissue manipulated between the two structures.

Figure 15:
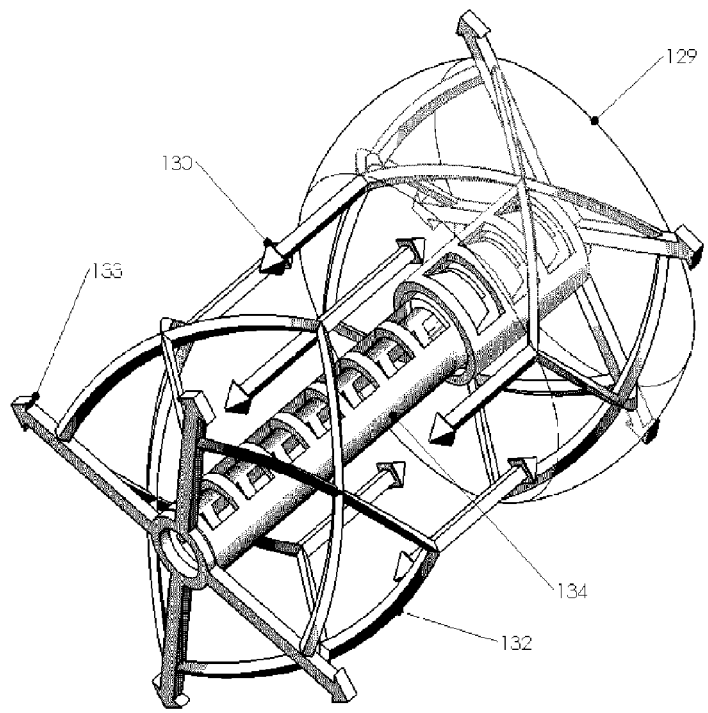
FIG. 15 is another version of an implant for the sequence shown in FIGS. 10-12. This version includes a central member connecting the proximal and distal members.

FIG. 15 illustrates another embodiment with the features of FIGS. 13 and 14 with an additional central ratcheting member 134. The central ratcheting member is included to facilitate shortening or lengthening of the fallopian tube 100 at the site of implant installation and twisting. The shortening or lengthening can be actuated before or after the tube has been substantially occluded. The shortening or lengthening during the implant procedure is intended to facilitate optimal closure of the lumen and the desired healing situation.

Figures 16A, 16B, 16C:
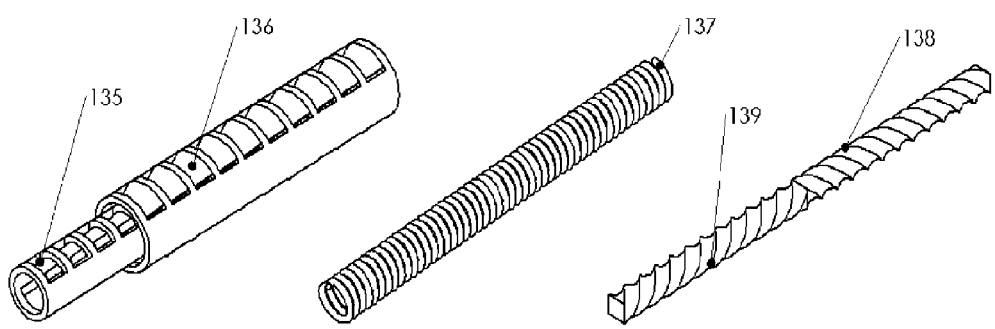
FIGS. 16A-16C show three possible types of central members having different mechanisms for changing distance between the proximal and distal members.

FIG. 16A illustrates an additional mechanism that could be utilized as a center lengthening or shortening mechanism. The inner ratcheting mechanism 135 interlocks with the outer ratcheting mechanism 136 to selectively telescope in or out to shorten or lengthen. The telescoping assembly ratchets and locks to the desired axially position. The spring mechanism 137, illustrated in FIG. 16B, can also transmit energy to the attached anchors to shorten or lengthen the assembly. The distal helical thread 138, illustrated in 16C, and proximal opposite direction helical thread 139 can be coupled to alternative anchors to shorten or lengthen the distance between the anchors with rotation of the central shaft element. A single helix can also be utilized if axially pinned to one anchor with the helical thread engaging the other. The central member could also consist of a any member that can span and link the two structures either rigidly or flexibly such as cables, strands, wires, tethers, extrusions, and anything else commonly used in the practice.

Figure 17:
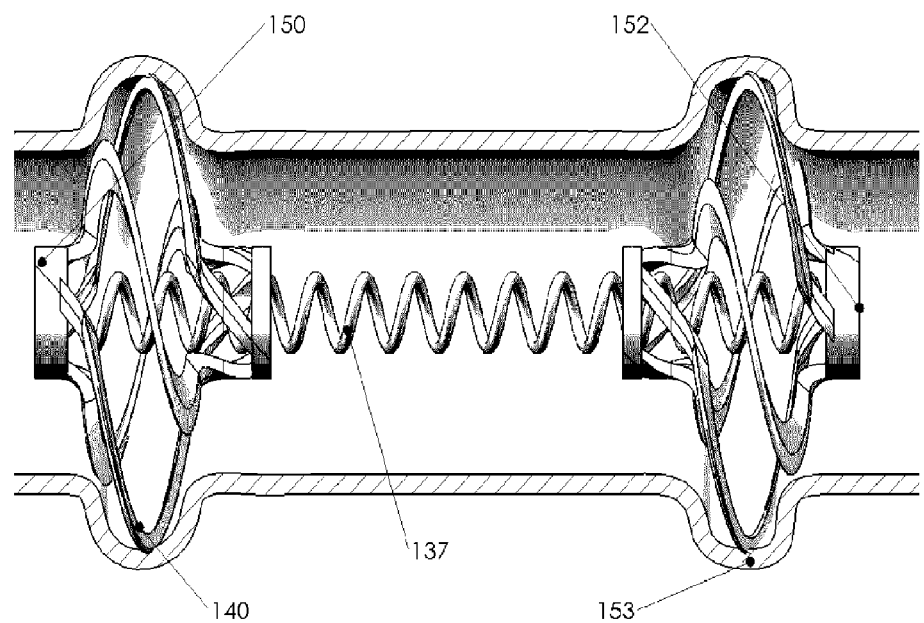
FIG. 17 is an early stage in the sequence of deployment of a device of the invention which has expandable anchor members and a spring central member.
Figure 18:
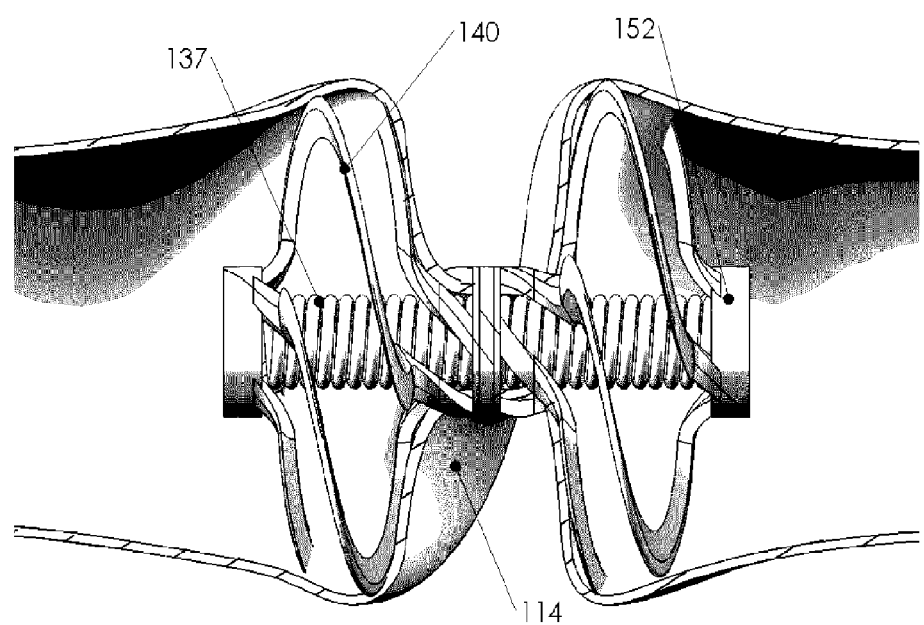
FIG. 18 is the next stage in the sequence of deployment for the embodiment of FIG. 17. The anchors have been drawn axially together.
Figure 19:
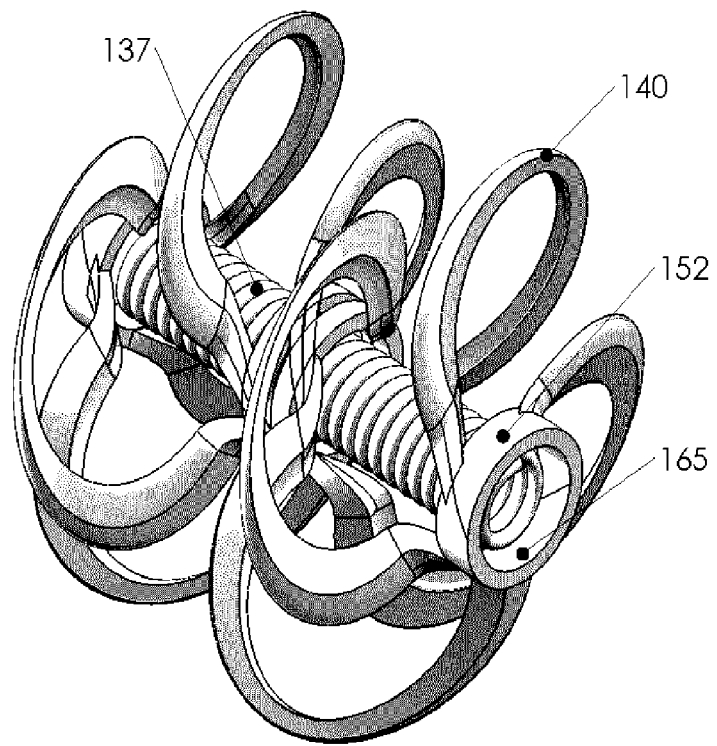
FIG. 19 is a three dimensional representation of the device described in FIG. 17 and FIG. 18.

FIGS. 17, 18, and 19 illustrate yet another embodiment consistent with the invention presented. The distal and proximal anchors are intended to engage and anchor to the fallopian tube wall. The anchors can engage the wall with radial pressure and/or engaging barbs or features. The central section is intended to lengthen or shorten, depending on the delivery sequence. FIGS. 17-19 show a unique expanding anchor that spirals open: helical expanding anchor 140. Also shown is the spring assembly 137 which acts to lengthen or shorten the anchor position and coupled tissue. Distal coupler 152 and proximal coupler 150 are designed to be rigidly fixed to spring mechanism 137, thus transmitting the appropriate axial and/or rotational force between the anchors and center section. The opposite coupler on the distal and proximal anchors 140 is intended to travel independent of the spring mechanism allowing free expansion of the anchors and movement of the anchors while the spring mechanism 137 travels back and forth within the central axis portion of the anchors 165.

Figure 20A:
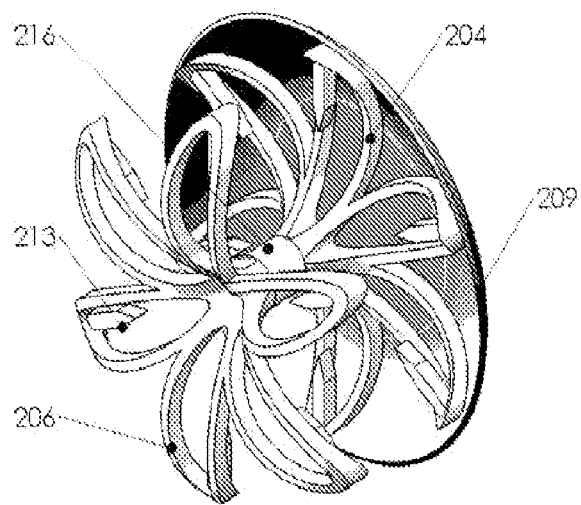
FIGS. 20A-20C show another embodiment of a device of the invention to hold tissue between the proximal and distal members to help create an occlusion of the lumen.
Figure 20B:
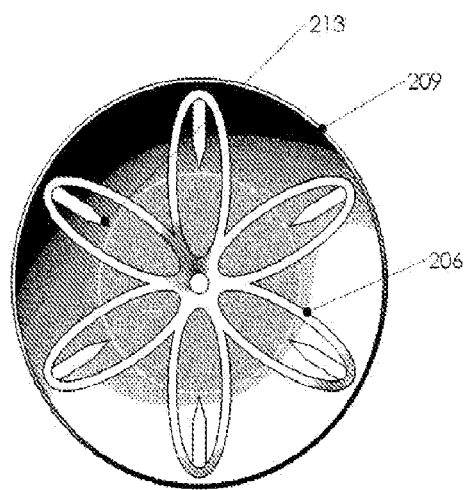
Figure 20C:
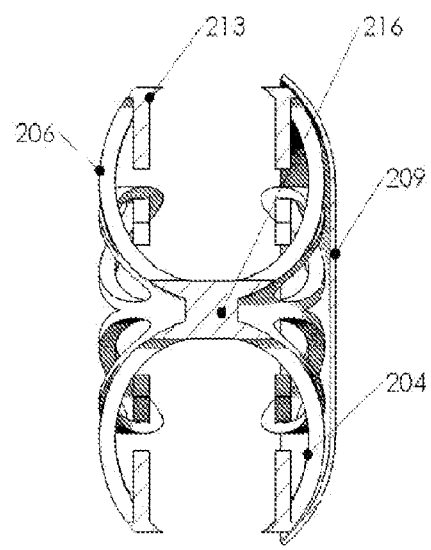

FIGS. 20A, 20B, and 20C illustrate a single unitary structure that has similar delivery and anchoring features to FIG. 1. The distal anchor 204 is released into a lumen, thus anchoring tissue with expanding elements that may or may not have barbed elements 213. The expanding members engage the tissue through an expansion similar to that of a flower petal motion, in which the tips expand radially from the axis. The user then applies a rotational force through the delivery apparatus, twisting the lumen closed. The proximal anchoring element 206 then released to engage and hold the twisted lumen in place. The central implant member may also have a torsion mechanism 216 capable of exerting rotational forces. The proximal or distal anchors or both may have a covering 209.

Figure 21:
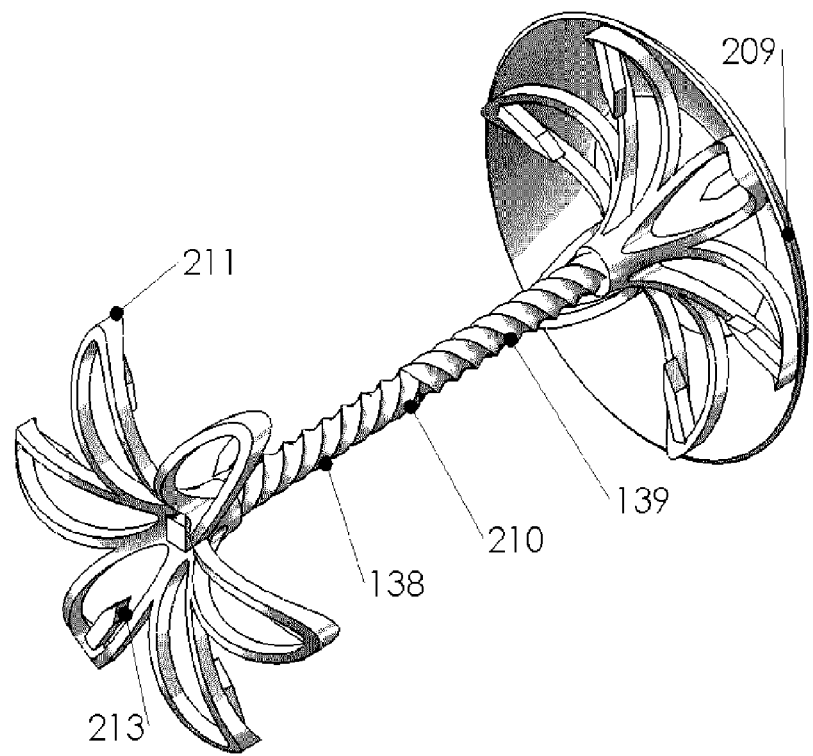
FIG. 21 is a device having proximal and distal anchors like those shown in FIG. 20 but mounted on a threaded central member to control axial distance between the anchors.

FIG. 21 illustrates an additional embodiment that has intended features similar to FIG. 17. The distal and proximal anchors are intended to engage and anchor to the fallopian tube wall. The anchors can engage the wall with radial pressure and/or engaging barbs or features. The central section is intended to lengthen or shorten, depending on the delivery sequence. The central member can also exert the desired rotational motion.

FIG. 22A illustrates yet another embodiment intended to occlude the fallopian tube. This embodiment has similar elements as described above, to anchor and twist the tissue. The primary difference shown in this embodiment is torsion elements connecting the anchor elements reside at the outer luminal surface, rather than in the center. The off-center torsion element 141 can be at the lumen surface or anywhere in between the center axis and lumen surface. The expandable anchor elements 132 engage and retain the lumen wall with or without the aid of the anchor barbs 133. FIG. 22B illustrates the expanded state of FIG. 22A. FIG. 22B illustrates the off-center twisted state of the embodiment. This embodiment could also be covered with of have material within its interior which would help facilitate the closer of the lumen as described herein.

Figure 23A:
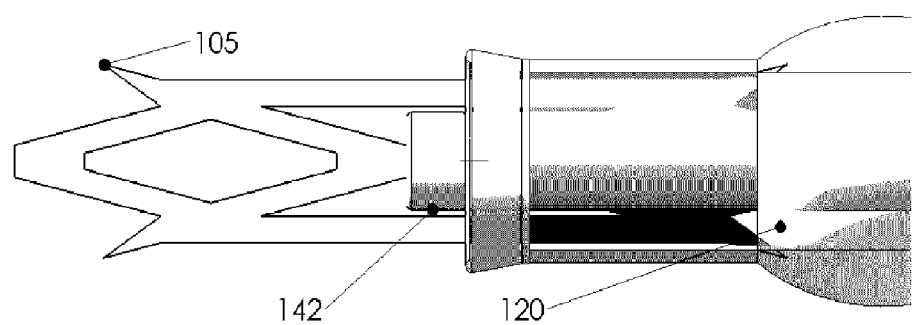
FIGS. 23A-23C show a sequence of deployment for an embodiment like that shown in FIGS. 22A-22F having a torsional control member extending from the delivery sheath to the distal anchor to actuate the torsion of the anchors relative to each other.
Figure 23B:
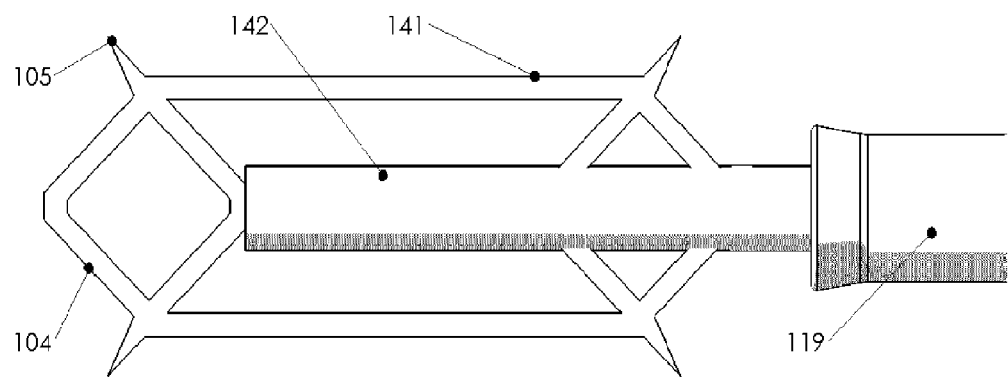
Figure 23C:
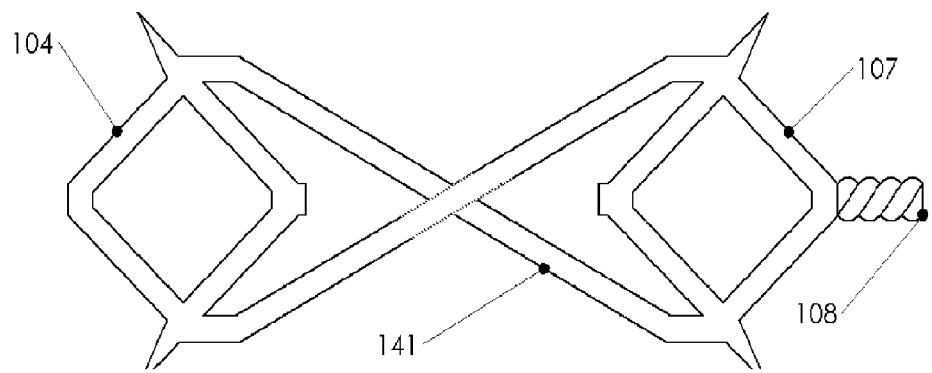

FIG. 23A illustrates another embodiment similar to FIG. 22. The distal and proximal anchors will engage the tissue while the off-center torsion element exerts rotational forces to occlude the tube. The distal anchor control mechanism 142 holds the distal and proximal anchors rotationally stable until the anchors are firmly expanded and engaging the lumen wall. Once the user is satisfied, the distal control mechanism 142 is retracted allowing the relative torsion between the anchors and occlusion of the fallopian tube 100. FIG. 23B illustrates both proximal anchor element 107 and distal anchor element 104 have engaged the wall of the lumen with the aid of the anchor barbs 105. The delivery tube 119 and proximal balloon anchor 120 are stabilizing the proximal fallopian lumen 102 before the off-center torsion element 141 is released. FIG. 23C illustrates the next stage of delivery in which the off-center torsion element has been released by the distal anchor control mechanism 142, thus allowing the lumen to be twisted into a substantially closed state.

Figure 24A:
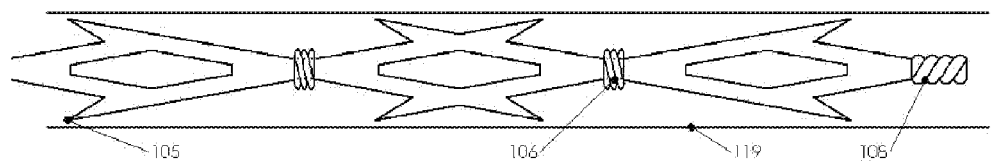
FIGS. 24A-24C show a sequence of deployment for an embodiment of the invention having 3 expandable anchor members deployed with stored torsional energy in the connecting members between them to twist the expanded anchors relative to each other.
Figure 24B:
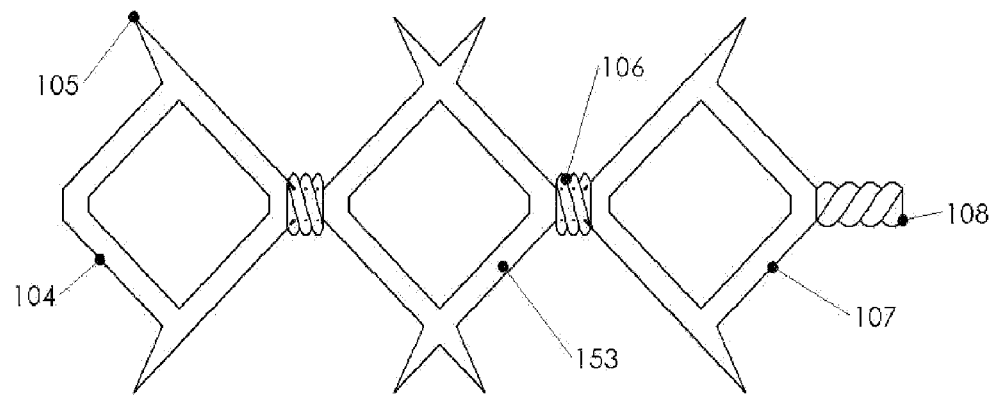
Figure 24:
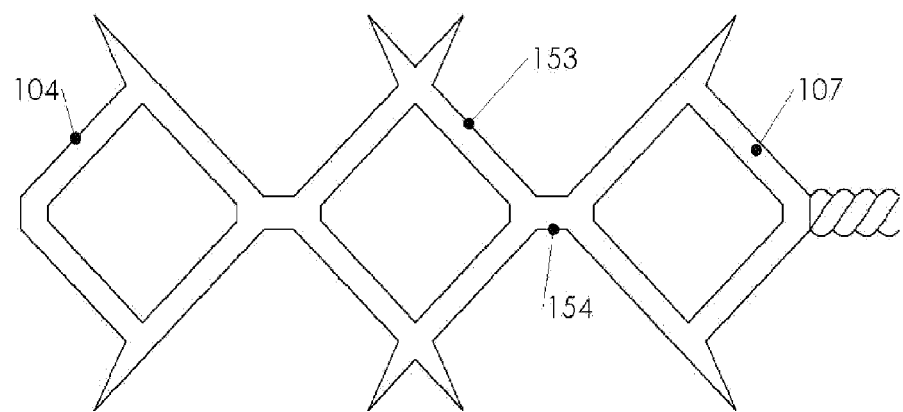

In another possible embodiment of this invention the implant can comprise three anchor elements instead of two. In this embodiment the end anchor elements would not be rotated relative to the lumen and the central anchor element would be rotated so that all twisting in the lumen would be localized within the length of the implant. This could be beneficial for decreasing concern of twisting of the fallopian tubes near the ovaries which can be painful for a patient. Procedurally this can be accomplished by first expanding all three anchors in place, and next using a keyed torquing shaft within the central shaft to selectively rotate the central anchor and to lock this rotation relative to the end anchor elements prior to decoupling the implant from the delivery system. Another approach would be to have a system that the central member was free to rotate relative to the proximal and distal members, allowing for the desired rotation to be delivered while the proximal and distal anchors were held stationary and then the assembly could be locked together permanently fixing the rotation. FIG. 24A illustrates an embodiment designed to isolate the bulk of the fallopian tube from the twisting forces being applied. Delivery tube 119 constrains the three part occlusion embodiment. FIG. 24B illustrates the next stage in the delivery sequence where the three anchor elements are expanded and in a configuration intended to engage and twist the lumen into a substantially closed state. The center anchor element 153 will rotate up to 360 degrees while the distal anchor element 104 and proximal anchor element 107 will engage and stabilize the respective proximal and distal lumens. Anchor barbs 105 can be present on all, none, or some of the three anchor elements depicted. FIG. 24C illustrates the three anchor element embodiment, with the three anchors able to rotate either substantially independently or in concert with each other such as to create a rotation in the tissue that closes the fallopian tube. This combination could be that the end anchors remain stationary and the middle twists or rotates. The middle member could also remain stationary while the end members twist. The action could be spring loaded with in the device or the mechanism could be activated thru the delivery system. All three anchors expand to engage and flatten the tube. The center section then is rotated creating a localized occlusion while isolating the rotational motion from the surrounding anatomy further removed along the fallopian tube.

Figure 25:
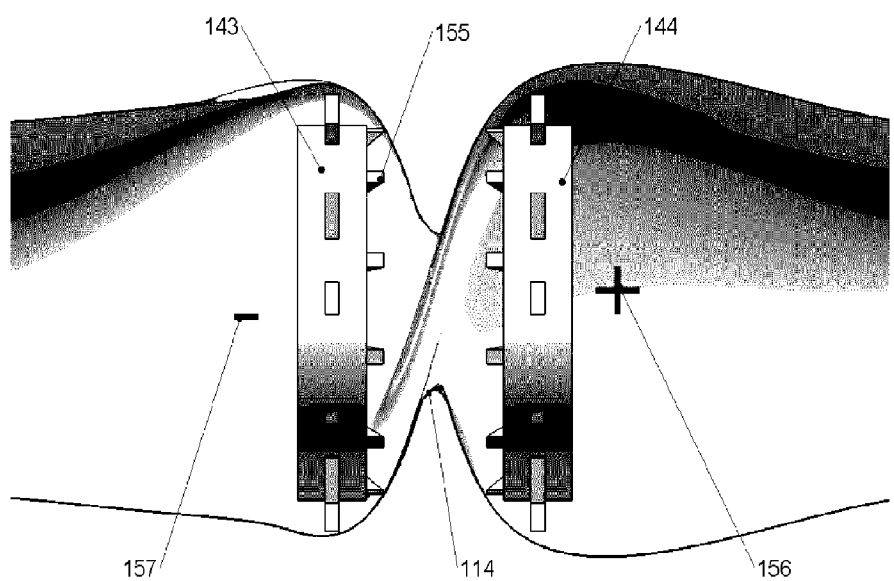
FIG. 25 shows a device of the invention with magnets in the proximal and distal anchor members.

FIG. 25 illustrates an anchor embodiment that utilizes magnetic forces. The proximal magnetic anchor 143 and the distal magnetic anchor 144 are held in close proximity to each other by magnetic attraction. The tissue can be occluded by rotational occlusion as described earlier and the magnetic anchors with piercing members 155 will hold the tube in an occluded and twisted state, twisted segment 114. The magnetic anchor may or may not include barbs to facilitate lumen anchoring. The magnetic anchors 143 and 144 could also have certain magnetic polarities 156 and 157 that could also facilitate the twisting of the vessel. The distal anchor could be deployed, and then the proximal anchor. Once both anchors are released from the delivery device, the rotational polarity of the anchor elements creates twisting and vessel occlusion.

Figures 26A, 26B:
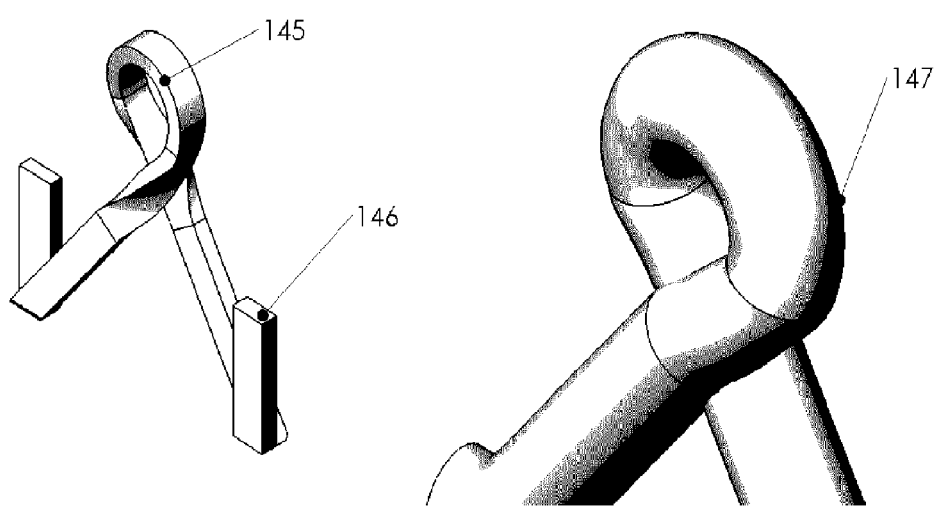
FIGS. 26A-26B show an embodiment of an implant which elastically deforms from a relatively straight configuration for introduction to a looped configuration when released to induce a loop in the lumen.

FIG. 26A illustrates an embodiment which utilizes a single ribbon shaped structure formed into a loop that will both anchor and twist the lumen into an occluded state. The ribbon twisting element 145 and ribbon anchor element 146 will be delivered in a substantially straight configuration into the fallopian tube 100. Once located in the correct orientation, the ribbon anchor element will be released or actuated to take the shape shown. FIG. 26B illustrates the fallopian tube from the external perspective with the ribbon shaped structure already installed and deployed. The result is shown as the ribbon embodiment twisting fallopian tube 147 which is an occluded configuration.

Figure 27:
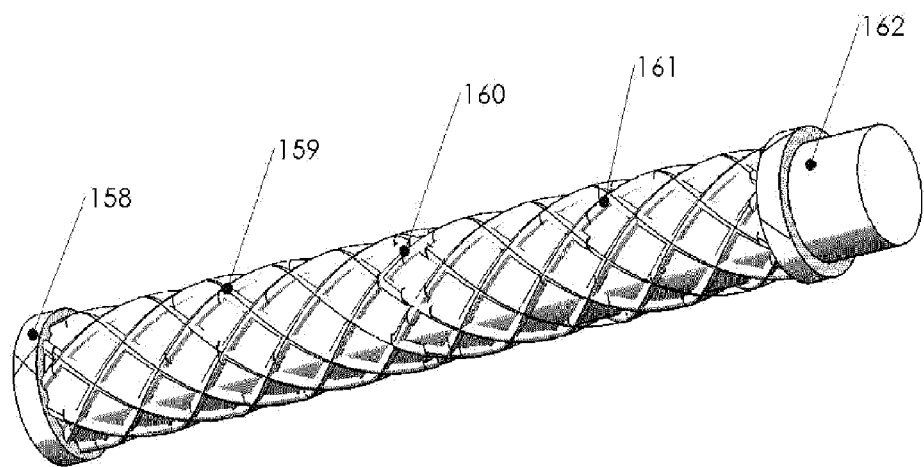
FIG. 27 shows the implant of FIG. 28 with the anchors in their collapsed state.
Figure 28:
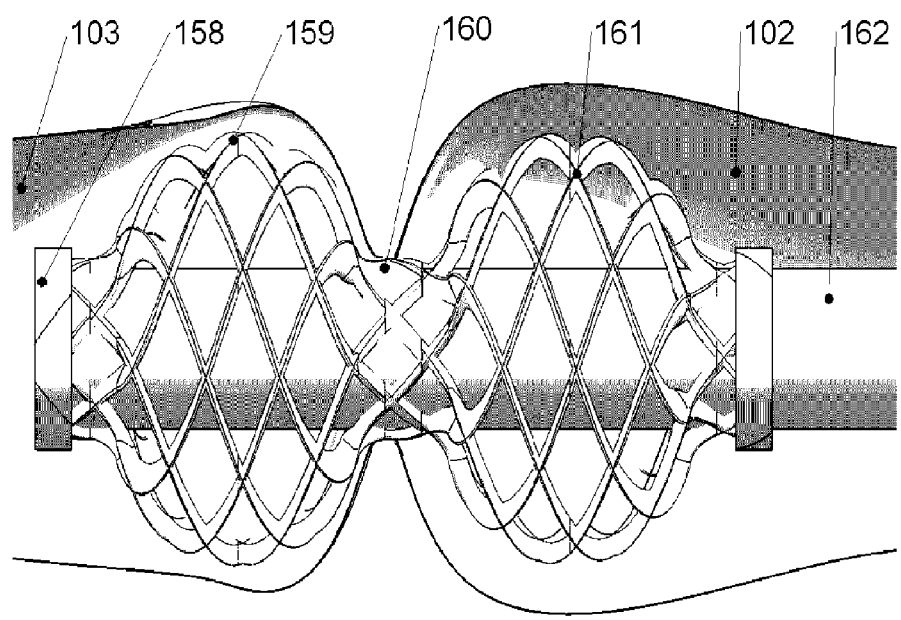
FIG. 28 shows an embodiment of an implant of the invention with the anchor members comprising a braid. The anchors are in their expanded state with the tissue twisted

FIGS. 27 and 28 illustrate another alternative embodiment intended to occlude a tubal structure. This embodiment works in the same way as those previously described. The anchors and central portion are configured from a braided wire or filament construction. The mechanism has a distal member 159, a central section 160, a proximal member 161, a distal member or cap 158 that attaches to the optional central member 162. The distal and proximal members can be constructed in such a way and out of such material that they primarily are in an expanded state in there resting configuration. In this expanded configuration the members can be designed to provide enough radial force to engage the fallopian tube 103 and twist it relative to proximal section 102. The structure could be constructed out of any material that would allow this expansion such as but not limited to nitinol, polymers, or any highly elastic and shape memory material. For this configuration the central member 162 is optional as it does not facilitate the mechanism of expansion. Conversely the same construction could be made out of other materials such as but not limited to plastically deformable filaments of stainless steel, cobalt chromium, titanium, copper, etc. With these types of filaments the central member 162 applies axial force along with the delivery system to the distal member 159 through 158 as to compress the braid and therein expand the diameter radially. This could be done in any number of sequences same as the other embodiments already described herein. The central member can then lock axially and rotationally to the proximal anchor member through any know mechanism that could accomplish such feature sets such as but not limited to keying, screwing, snap fit, ratcheting, etc. Finally the implant is disengaged from the delivery system via any of the already disclosed methods. The entire structure could also be covered with or encapsulate a material that would facilitate both acute and long term closing of the tube such as those previously described and including but not limited to polyester, collagen, or any other material that facilitates ingrowth of tissue into and around the structure.

Figure 29:
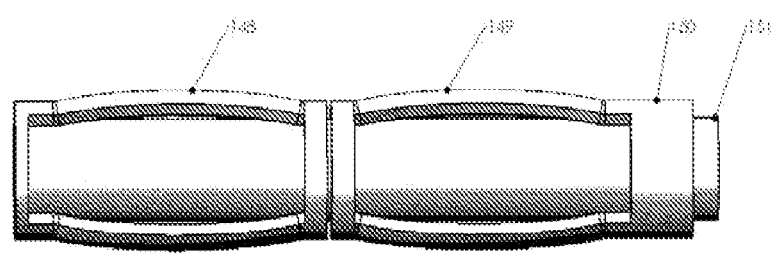
FIG. 29 shows an embodiment of an implant of the invention where the proximal anchor member can be independently rotated over the central shaft member which is rotationally fixed to the distal anchor member. The anchor members are shown in the reduced diameter state.
Figure 30:
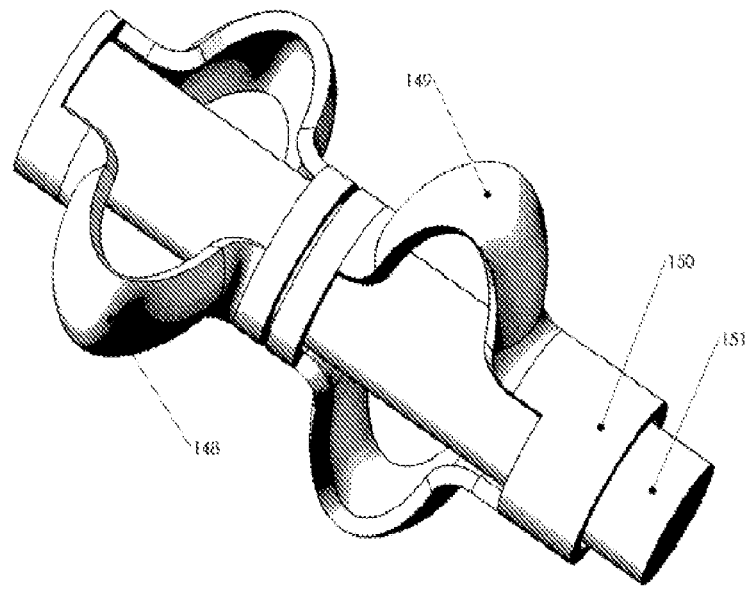
FIG. 30 shows the same embodiment as FIG. 29 with anchors expanded and twisted relative to each other.
Figure 31:
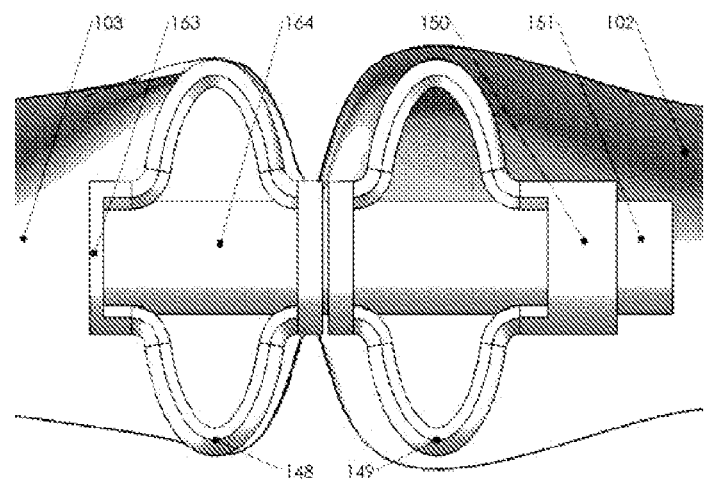
FIG. 31 shows the same embodiment as FIG. 30 with the device shown in a tissue lumen.
Figure 32A:
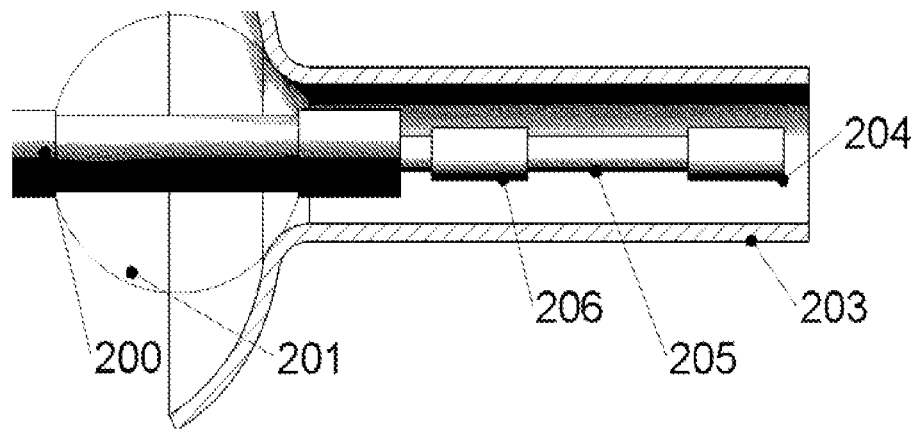
FIG. 32 shows a deployment sequence of the invention which has proximal and distal anchor members which expand to engage the lumen wall and then are axially drawn together to bunch/plicate the tissue of the lumen.
Figure 32B:
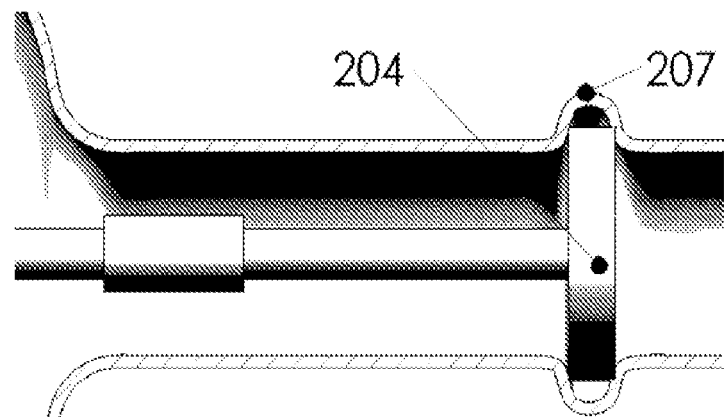
Figure 32C:
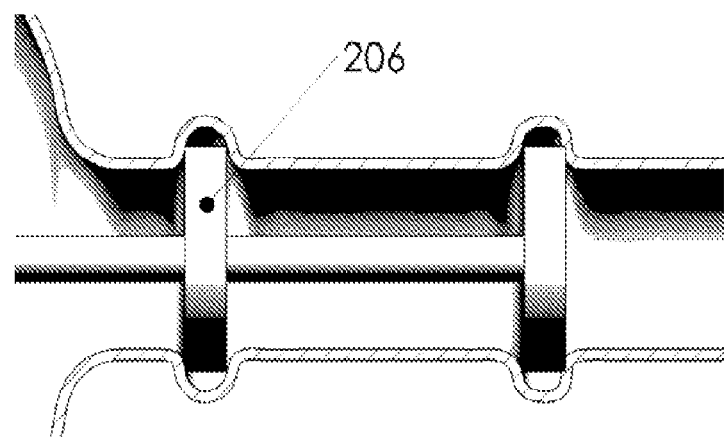
Figure 32D:
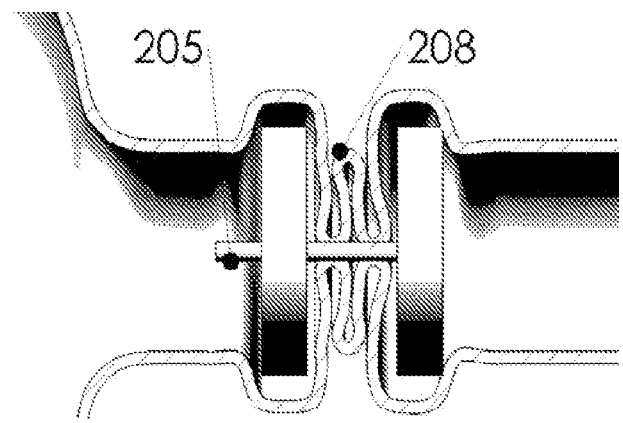

Another related embodiment of this invention alters the sequence of the deployment steps to yield the twisted lumen result anchored with the implantable device. For this specific embodiment, the distal anchoring element is first positioned and expanded as described earlier. Second, the proximal anchor element can be expanded to engage the tissue of the lumen wall. Next one of the expanded anchor elements is twisted relative to the other anchor element by transmitting torque to the anchor element through the central shaft. This will result in the anchor elements twisting the lumen creating the tissue seal over the central shaft between the two anchor elements. This twisting in the central shaft can be accomplished with central shaft which is torsionally fixed to both anchor elements and which has stored torsional energy when introduced which can be released after expansion of the anchor elements. It also can be achieved by means of having the distal anchor element torsionally fixed on the central shaft with the proximal anchor element rotatable over the central shaft. In this case the rotation of the proximal element over the central shaft can be separately actuated with an independent torquing element in the delivery system and with means included to lock the proximal anchor element to the central shaft after rotating the proximal anchor element in order to lock in the tissue twist before decoupling the delivery system from the implant. FIGS. 29, 30 and 31 illustrate separately controlled distal and proximal anchors that can be independently controlled, keyed and locked together. Distal anchor 148 can be expanded to engage the lumen. Proximal anchor 149 can be independently expanded to engage the proximal lumen. The inner control tube 151 controls the distal anchor 148. The outer control tube 150 controls the proximal anchor 149. The rotational and axial spacing and orientation between the anchors can be changed and subsequently locked together to fit the variable needs of the anatomy. The members of this configuration can incorporate any and all of the already described embodiments such as barbs, piercing elements, covering, etc. . . .

In another embodiment of the present invention, the implant acts to shorten the lumen and the resulting bunching or plicating of the walls creates an acute blockage in the lumen. In this embodiment a distal anchor component is expanded to engage with the wall of the lumen. This distal anchor element may be similar to the distal anchor elements described earlier except that now it is acting to move the lumen axially instead of rotationally. A second proximal anchor may then be expanded inside the lumen at a point proximal to the distal anchor with a central shaft connecting the two anchor components. The two anchor components are then drawn towards each other along the central shaft which has the effect of plicating or bunch/plicating the lumen wall between the anchor components. This acts to pack the wall folds together to yield an effective occlusion of the lumen around the central shaft of the implant. The anchor elements are then axially locked in their respective positions on the central shaft. Finally, the delivery system can be decoupled from the implant and withdrawn. FIG. 32 depicts this for mentioned embodiment of the invention. The figure demonstrates another possible way to manipulate a tubular tissue structure or vessel, such to shorten, fold and/or plicate along the axis so that the interior lumen is in intimate contact with itself and the opposing side, such that the vessel is no longer patent, such as sealing closed a fallopian tube.

The first step from FIG. 32 is optional meaning it is not necessary to achieve the desired effect. A mechanism 200, consisting of an outer catheter with a balloon or expanding device on the outside of it, is introduced. The outer device with a stop 201 that serves as a depth gauge is introduced into the uterus 202 and then into the fallopian tube 203 up to the point where the stop contacts the uterine wall at the ostium of the fallopian tube. This catheter has several features which make it unique. It could be shaped to more easily access the ostium of the fallopian tubes. It could be articulating to better accommodate a larger range of anatomy. The catheter has an expanding device 201 near the proximal end which serves several purposes. The expanding device acts as a depth gauge for the distal end of the catheter. The expandable member is expanded and the catheter is inserted into the fallopian tube until the expandable member reaches the ostium. The distance from the expandable member to the tip of the catheter is known and can be modified accordingly and therefore can be used as an exact location device inside the fallopian tube where visibility is limited. The stop could be constructed from a balloon, a wire mesh, or other structure that can engage and prevent further progress of the delivery system into the vessel distally. This prevents the vessel from being manipulated in areas that are not desired. This also allows the tissue to be manipulated in a desired area. The structure could be that of a balloon, stent, or a radially expanding member that can generate sufficient force against the tissue wall such that enough friction or holding force is generated to retain the tissues position. This feature also facilitates easy removal of delivery device by radially unexpanding the engagement feature. It also helps limit the area on which the desired tissue manipulation is acted. It also facilitates visualization of the tissue being manipulated by expanding the lumen. If said structure forms a seal against the tissue then it also facilitates a method in which other therapy or diagnostics could be administered, such as; pressure, drugs, thermal, liquids, visualization aides, sclerosing agents, and or a patency test post tubal occlusion. This can be done before, during, or after each step of the process of tissue manipulation as described herein.

The mechanism also has an inner catheter with a balloon or expanding device on its outside. The inner member can move relative to the outer member. The expansion devices provide sufficient force against the tissue of the lumen in which to engage and manipulate it. The expansion device can be used for gathering, plicating, inverting and or twisting the tissue of the lumen. The expansion device can be used to deliver other devices. The expansion devices could be used to deliver therapy such as heat, cold, radiation, drugs, etc. The expansion device could be used to assist visualization. The expansion device could form a seal with the tissue. This seal could then facilitate the delivery of fluid or gas to the tissue in a desired location in a controlled manner. This seal could facilitate the use of positive or negative pressure to manipulate the tissue. These items could all be used alone or in conjunction with each other.

Secondly a separate or independent member of the assembly is advanced axially and distally into the desired location in the vessel. The expanding members are introduced into the lumen of the vessel in an unexpanded state 204. A distal expandable member 204 is then activated such as to engage the tissue in this desired location. The distal expanding member is expanded and engages the tissue of the vessel sufficiently enough 207 to impart a manipulating force upon the walls of the vessel tissue. This member could be constructed from any axially expandable structure that can generate sufficient force against the tissue wall such that enough friction or holding force is generated to manipulate the tissues position, such as a balloon, stent, or radially expanding member such as those depicted in this invention.

The next two steps can be done in multiple arrangements. These sequences all accomplish the same desired net effect of plicating the tissue. The order of expansion of the anchors and shortening of the distance between them and the delivery system can take place in multiple configurations with the same end state. These descriptions herein describe some possible configurations, others exist. All possible methods to obtain the net result of plicating, twisting, folding, flattening, or otherwise reducing the lumen area to effectively close the lumen of the vessel are thus encompassed in these descriptions as to not create an endless list of possible series of steps. Such examples include but are not limited to:
1. Insert delivery system and implant 32A, engage/expand distal anchor 32B, engage/expand proximal anchor 32C, manipulate tissue, and release implant 32D.
2. engage/expand distal anchor, manipulate tissue, engage/expand proximal anchor, and release implant.
3. engage/expand proximal anchor, engage/expand distal anchor, manipulate tissue, and release implant.
4. engage/expand proximal anchor, engage/expand distal anchor, release implant, and manipulate tissue.

These examples also apply to all of the embodiments encompassed in this invention. A second proximal axially expanding engaging member 206 is then deployed. The distal expanding member and proximal expanding member are now expanded and engage the tissue of the vessel sufficiently enough to impart a manipulating force upon it. The two members are then brought together axially, i.e. the distance between the two members is shortened. This action in combination with the members engaging the tissue originally contacted, plicate the tissue 208 such that the tissue closes the lumen by tissue to tissue contact. The plication of tissue fills the space or volume of area completely and the tissue is in intimate contact with all open lumen area being consumed by the volume of tissue that is being forced into the remaining area between the two anchors. This bundling or plicating tissue or vessel wall effectively reduces the working lumen area to zero and the vessel lumen is no longer patent, preventing anything from passing from the distal to proximal end of the vessel, or proximal to distal.

The central member 205 between the two expanding members is constructed such that movement between the two anchors can be reduced. This construction could be two members which nest and slide axially, a threaded member that engages the anchors, an axial spring, an elastic member that is allowed to reduce, or any other construction that allows for this action of reducing in length. The member can be fixed to one or both or neither of the anchors. The member could be constructed to be removed from the assembly. The member could be constructed such that no fluid could pass axially through it or along it.

FIG. 32 is a representation of any expandable distal 204 and proximal 206 tissue engagement members. These members can be composed of any radially expanding structure including but not limited to a stent like structure, balloon, wire mesh, etc. The expansion can be activated axially, radially, bending, rotationally, torsionally, plastically and or any other method of moving from one state to another. The central axial member 205 is capable of imparting force to the distal and proximal members independently in both an axial and rotational directions. The member can then lock or become fixed, retaining the forces imparted onto the tissue for an indefinite period of time. The final state of the assembly could be one no residual stress, or conversely that of a condition of stored energy, or one of stored stress and energy. The assembly could exist with or without a central member. The proximal and distal members could possess barbs to engage the tissue substantially perpendicular to the axis. The proximal and distal members could possess piercing elements to engage the tissue axially. The proximal and distal members could possess materials that imparted forces on each other such as magnetic force to attract, hold, and/or rotate relative to each other and the central member and delivery system.

The actions described can be done independently or in combination with the twisting action previously described herein. These forces can be generated by the delivery system and transferred from a handle set to the anchors. The distal and proximal anchor can be activated by members in the delivery system that transfer the forces needed to foreshorten the distance between the anchors. This action could be that of twisting, rotation, axial force, or other moments of force needed to accomplish the desired affect. One skilled in the art could easily construct a delivery device which could employ said needed forces upon the anchors to effectively activate the desired motion. The delivery system could work in conjunction with features on the engagement anchors to achieve the desired motion. One possible method of rotation provided by the delivery system could be imparted onto the central member and or an anchor such that a threaded mechanism would then be activated in such a way to create an axial motion of the members toward each other, shortening the distance between the distal and proximal anchors. Another method could be that linear motion on the handle could be transferred through members in the delivery system to the central member and/or anchors to achieve the desired motion.

The force could be generated by the expanding engaging member itself. The central member could be constructed in such a way that it can achieve the desired motion. One possible construct is the central member is constructed of an axial spring that is allowed to contract upon delivery. Another possible manner to achieve the desired motion is that there is stored rotational energy in the central member or anchors that is released and allowed to activate a mechanism such as a screw thread the achieve the desired motion. The delivery device can then be separated or decoupled from the tissue engagement feature. Several mechanisms described herein could be utilized to achieve this effect such as but not limited to screw, friction, pin, ball joints.

Additional visualization, therapy delivery, or diagnostic testing can then be preformed. The delivery device can then be removed leaving behind the tissue manipulation device.

Depending on the nature of the tissue manipulation the device could be removed at this stage also leaving the tissue permanently manipulated. One such example of this includes but is not limited to therapy being delivered to the tissue during its reduced state, compressed or plicated and/or rotated state. Such therapies include but are not limited to heat, ultrasound, sclerosing agents, cold, chemicals, adhesives, polymers, radiation, any activity that could damage the tissue, induce a healing response, bond the tissue together, or otherwise change the initial state of the tissue.

Figure 33:
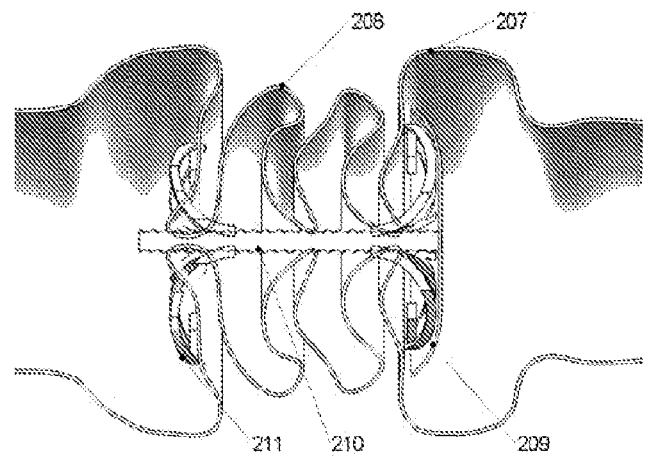
FIG. 33 shows another embodiment of a device to bunch/plicate the lumen tissue as shown in FIG. 32.

FIG. 33 depicts another embodiment of the invention depicted in FIG. 32. This embodiment shows in detail an assembly mechanism that can accomplish the effect described herein. The figure depicts a vessel in a plicated state 208 with an implant assembly mechanism that both obtained said plication upon delivery and will maintain said plication indefinitely, effectively closing the lumen of the vessel to any passage of matter. The implant assembly mechanism consists of a distal tissue engagement anchor 209 with a covering, a threaded central member 210, and a proximal tissue engagement anchor member 211.

The distal member here and earlier depicted consists of features that expand from the central axis of the device in an angular or curving manner. The members could be described as being similar to in looks and motion as flower petals opening. The opening members could be in number from one to infinite. These members could be constructed of a shape that imparted enough friction force upon the lumen wall tissue to engage it, such to allow manipulation of said tissue in an axial and or rotational manner. There could be additional tissue engagement features upon the expanding members to actively engage the tissue such as barbs, hooks, or pierce points that would actively engage the tissue wall of the lumen, effectively increasing the amount of force that can be imparted onto the tissue by the member. The figure depicts barbs that can extend from the distal ends of each of the expanding radial members. These barbs effectively point toward the wall of the vessel upon expansion of the radial member. The barbs then engage the vessel wall tissue. The final state of the barbs is such that they hold onto the engaged tissue by being substantially pointed back toward the axis of the lumen, thus not allowing the captured tissue to be released form the barbs. The central portion of the distal member is engaged onto the central member. This engagement could be that of permanent fixation. This engagement could be that of a moveable mechanism. Such movable mechanism could be that of a threaded screw like mechanism. The member could be constructed of any such elastic or plastically deformable material that is implantable in the human body. These materials include but are not limited to nitinol, metal, steel, plastic, thermo polymers, etc. The surface of the members could be such as to promote healing to permanently close the lumen. Conversely the surface could inhibit growth thus facilitating removal of the device. They could either be coated with materials to activate tissue ingrowth or eliminate such ingrowth. The distal side of the distal member is covered with a flexible membrane that serves to further block or seal the lumen of the vassal. The membrane is attached to the distal member. The membrane could be constructed of any material that would promote either acute or permanent sealing of the lumen. Such materials could be chosen to produce the desired effect and include but are not limited to, polymers, silicones, Teflon's, eptfe, ptfe, Dacron, polyester, urethanes, tissue, collagen, tissue scaffolds, etc. These membranes could thus also be coated or impregnated with other substances to achieve a desired response of either healing or not. These substances include but are not limited to sclerosing agents, adhesives, growth factors, drugs, etc.

The central member 210 depicted in FIG. 33 is a threaded rod like device that engages the distal member, proximal member and the delivery system. The threads are similar to a screw thread and could be in multiple rotation directions depending on the desired effect. The threads could be such as to activate motion of both the distal and proximal members toward each other through the rotation in a single direction. It could also be thread as to more one of the members and not the other. The member could have features on the proximal end to engage the delivery system. The central member could be fixed to either the proximal or distal expanding anchor members or neither. The central member could be free to rotate but substantially captured by either of the anchors or neither. The construction of this member is solid as to not allow passage of matter along the length of its axis. The surface of the structure could be treated in manner to facilitate a desired tissue response, either that of ingrowth or not.

The proximal member 211 depicted is similar to that of the distal member. It is not shown with a covering but it could certainly employ such a feature. The proximal mechanism can also have all of the features described herein.

Figure 34:
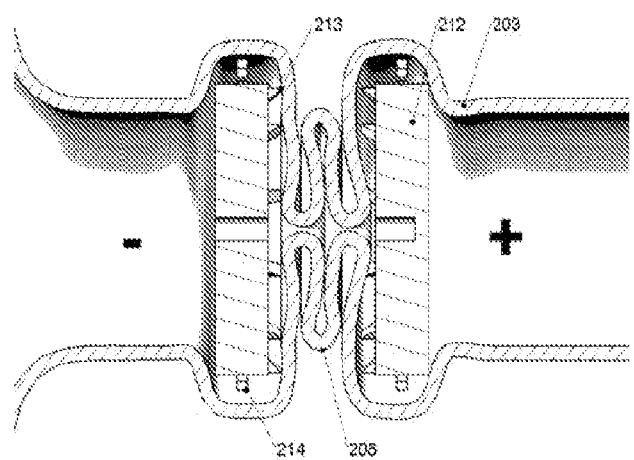
FIG. 34 shows another embodiment of a device like those shown in FIG. 32 and FIG. 33 which includes magnets in the anchor members.

FIG. 34 depicts another embodiment of the invention with the tissue in cross-section 203 in a plicated state 208 and with the implant in its delivered state. The implant has distal 212 and proximal members. The distal member 212 is constructed such that there is no continuous lumen. The shown implant has radially expanding engagement features 214 with a representation of tissue engagement features that engage or pierce into or through the tissue of the wall of the lumen assisting or increasing the amount of retention force that the engagement member imparts on the tissue of the lumen. These engagement barbs or features could be barbed, hooked, or needle-like. Additional engagement features in an axial plane 213 that further assists the amount of force that can be applied to the tissue during twisting and or placation. The figure also shows a representation of no central member present. The central member could be removed after ideal placement of the implant is achieved. It could also be maintained. The removal of the central member facilitates tissue to issue contact which will help achieve closure of the lumen. Another option is that a feature could pierce through the lumen tissue wall from the proximal member into the distal member, thus helping to retain position, this is not shown here, but has been shown in previous figures. The anchoring members could also be constructed from magnetic material that could exert sufficient force to maintain position of said implant in the plicated or twisted state. These methods could effectively retain said tissue in its manipulated state.

Figure 35:
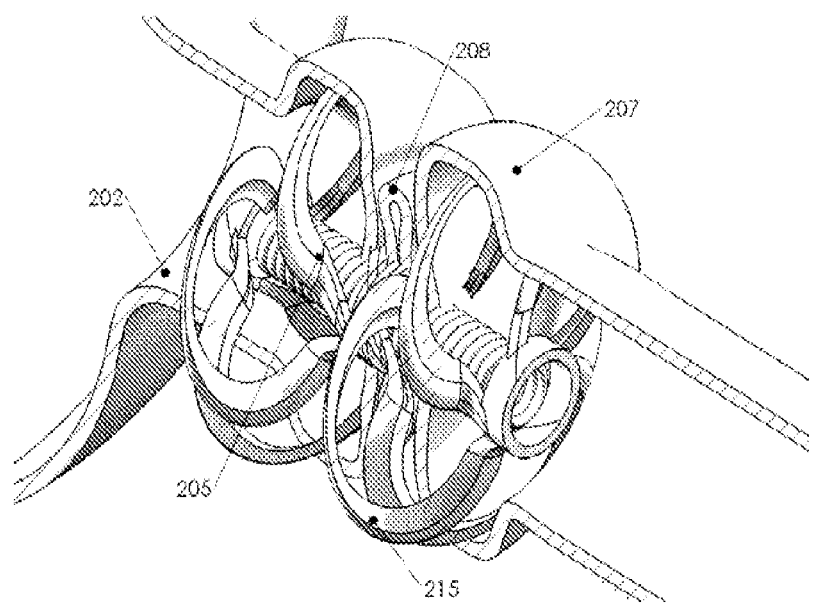
FIG. 35 shows another embodiment of a device like those shown in FIGS. 32-34 but having radially expanding anchor members.

FIG. 35 depicts an isometric, cross-sectional view, of vessel tissue shown as plicated and an implant with rotationally activated radially expanding engagement features. The proximal and distal anchors structure is capable of engaging the tissue of a lumen through expansion. 207 The structure is also capable of placating and/or twisting the tissue 208 as such to close the lumen. The distal and proximal anchors have members 215 that are shown radially expanded through rotation. The expanding members activated either through rotational or compression forces. The radial members are constructed in such a manner that when a compressive force is applied axially the members expand in a rotational manner. The expanding members could be plastically deformed into this expanded state. The members could be elastic and held under load in this expanded state. The expanding members could be set in this state and allowed to resume this expanded condition from a collapsed condition that would facilitate delivery. The construction material of the expanding members can be that of any implantable device including but not limited to nitinol, steel, plastics, etc. The members could be made from a continuos structure such as a tube. The members could be made of wire, ribbon, or any other shape and thus joined together to facilitate such a structure. These members can have features on them to further aide tissue engagement such as barbs or hooks. The central member 205 is shown in an unexpanded state. This central member is capable of applying both twisting and shortening force to the rotationally radially expandable engagement features. The central member lumen is filled with another structure that fills the area completely as to eliminate any passage of material from end to end. All other central members described here in could be employed with this configuration of anchors. Like wise any combination of members described herein could be used with each other to achieve the desired tissue manipulation.

Figure 36:
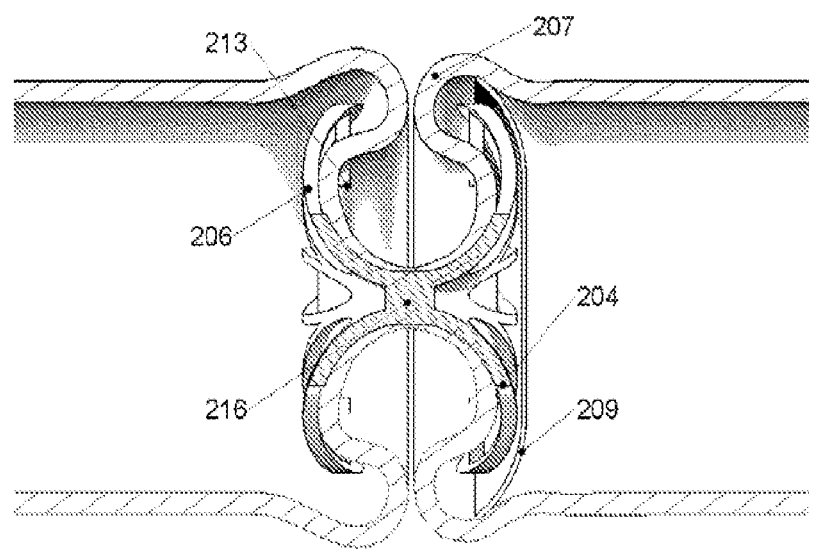
FIG. 36 shows another embodiment of a device like those shown in FIGS. 32-35 but having anchor members which expand radially with a set of petals which curl up from closer to the central axis of the device to their expanded diameter state.
Figure 37A:
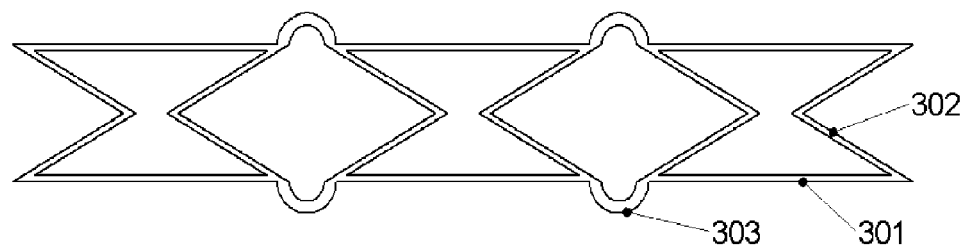
FIG. 37 shows an embodiment of the invention which has an implant including three flat expandable anchor members connected by curved connecting elements which acts to flatten and fold the lumen across its axis when implanted.
Figure 37B:
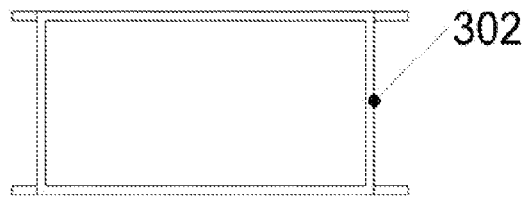
Figure 37C:
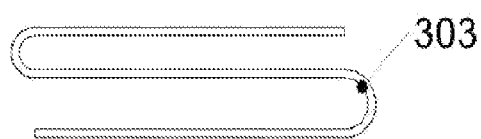
Figure 37D:
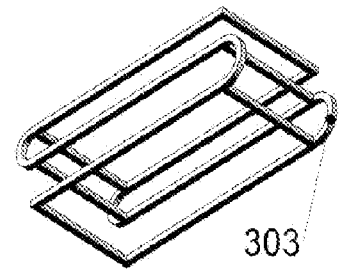
Figure 37E:
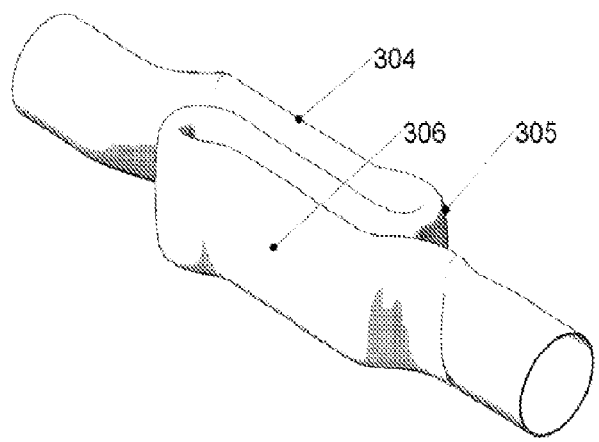

Another possible embodiment of the present invention is that the proximal and distal anchor elements are fixed in their location on the central shaft and that the axial gathering of lumen wall and consequent shortening is the result of pedal shaped anchor elements released for both the proximal and distal anchor elements. These pedal shaped anchor elements first engage the tissue of the lumen wall at points axially removed from each other and then pull these engagement points together as the pedals of the anchor element continue to curl back towards each other. FIG. 36 depicts a mechanism consisting of two sets of expanding members 204,206 on a single toroidal structure similar to that shown in FIGS. 20 and 34. The view is shown in cross section. The construction of the device could be that of made from one single unitary structure, such as a tube. The central lumen of the device is thus filled or plugged to facilitate closure of the lumen 216. The expanding members could have tissue engagement features 213 as shown here. One or both of the expanding members could have a covering as shown here. Such covering 209 could be flexible yet impermeable, such as ePTFE or other material. The delivery of this device is the same as described herein. Being a unitary structure could simplify construction and delivery. The distal members could be expanded from the delivery system, the tissue of the wall would then be engaged, the desired tissue manipulation takes place, and finally the proximal anchor is then released from the delivery device, and it engages the tissue and locks the manipulated tissue in place.

In another embodiment of the present invention, the implant acts to flatten and fold the lumen upon itself to create an effective tissue to tissue block of the lumen. In this embodiment, the device has expandable wings which act to flatten the tube due to the expansion of the wings in opposite directions. These wings can be self expanding frames cut from nitinol sheet constrained to a reduced size for introduction. In this embodiment, there can be two or more discrete flattening wing sections in a row along the axis of the implant. These wing sections are coupled and may have preformed tight radius bends in the coupling region between the two wing sections. These bends have the effect that when in the relaxed state (no stored elastic deformation), the two wings of the implant will be in an acute angle relative to each other. These bent coupling regions can be made of a highly elastic material such as nitinol to enable a high level of elastic deformation and corresponding spring force to return to its relaxed state. For introduction in to the body lumen where it is to be implanted, the implant can be straightened and compressed. This can be done with a constraining sleeve having appropriate axial stiffness to overpower the inclination of the implant to expand and bend. The implant is first introduced in its straightened and compressed state. The wings may then be released by pushing the implant out of the constraining sleeve which both flattens the tube and releases the constraint on the bend in the implant to allow the two wing sections to fold up creating a crease in the flattened lumen. This creates a block in the tube with the tissue to tissue contact brought on by the flattening and folding of the lumen. It would be possible to select the size of the wings to target a specific known size relative to the size of the lumen to be occluded. It would also be possible to size the wings to cover a range of lumen sizes possibly with a low expansion force so that one size can fit many lumen diameters with a low residual force on the lumen wall after expansion.

In another variation of this embodiment, the release of the wings for expansion and the release of the bend in the implant can occur with two separate actuations. One possible means of doing this would be to first release the expansion of the wings by pushing the implant out of a sleeve as described above. Then secondly to release the bend in the implant by withdrawing a stiffening mandrel axially pinned through keyways along the wings of the implant to hold it relatively straight.

In another variation of this embodiment, magnets can be incorporated into each of the wing sections so that they are drawn together and help hold the folds in tight proximity when the sections fold together. A mechanism such as this could enable the bend or bends in the implant to act more as hinges and not have to be the primary force drivers folding the lumen upon itself.

In another variation of this embodiment energy can be applied between the two wings in a bipolar fashion or from the whole implant in a mono-polar fashion in order to induce a healing response and consequent tissue ingrowth as described above.

In another embodiment of the present invention, a simple wing structure as described above can be used to flatten the lumen and this flattening can facilitate the tissue to tissue seal without the folding, twisting or bunch/plicating described earlier. As with the other modes of creating the tissue to tissue reduction in lumen opening, the earlier mentioned methods of energy delivery, inflammatory material, spermicidal or ovacidal materials may be used in conjunction with this implant to facilitate the long term occlusion of the lumen or to help functionally block the lumen until it has healed closed.

FIG. 37 depicts one embodiment of the invention just described. This method and mechanism for closing the lumen of a vessel consist of folding the vessel perpendicular to the axis of the lumen. The method is to flatten the vessel bringing tissue to tissue contact under tension and then to crease the lumen along the axis. This action reduces the effective lumen completely, to acutely and permanently close the vessel. FIG. 38 depicts a mechanism that could flatten and fold the tissue of a lumen perpendicular to its axis 37D. The figure consists of a representation of a mechanism in two views 37B 37C, and isometric view 37D and a planer representation 37A, and finally a representation of a lumen reduced or folded with said device 37E. The mechanism expands planerly thus flattening the vessel. It also folds out of plane perpendicular to the long axis such as to manipulate the tissue to reside against itself in intimate contact. The mechanism expands and folds in three dimensions. The mechanism could be spring activated. It could also be deformed into this shape by the delivery device and it could retain this shape. The folded assembly could retain its position through spring force, material strength, magnetic attraction, or other. When the folding is complete the external and internal tissues are in intimate contact with each other. Number 301 depicts the mechanism shown in number 303 in its planer representation. The depicted mechanism folds twice, however the same result could be obtained from a mechanism that only folds once, or three times. Number 304 depicts a tubular tissue structure or vessel that has been folded perpendicular to the axis with two folds so that the interior lumen is in intimate contact with the opposing side, such that the vessel is no longer patent, such as sealing closed a fallopian tube. The top planer representation of the mechanism 301 shows a feature that would facilitate the flattening of the lumen of a vessel 302. This feature allows the device to be compressed for delivery into the vessel by elastically absorbing the strain imparted on it by compressing the sides of the structure and therefore effectively make the angle shown more acute. Feature 303 depicts a hinge of mechanical device that allows for the folding motion depicted in the isometric view. This mechanism could operate like a spring. It could also be plastically deformed to achieve the final desired geometry. The representation of the vessel 304 shows the effect of the mechanism on a lumen. The members 302 imparted a flattening force on the vessel 306. Member 303 then imparted the creasing of the tissue 305.

FIG. 38 depicts another embodiment of the invention in which the device folds the tissue of a lumen axially 38B. The mechanism has tissue engagement features 310 at the location of bending. The mechanism expands 307, flattens the vessel 37A, engages the tissue, and then folds the lumen axially 308. This action brings the inner tissue of the lumen in intimate contact with itself effectively closing the lumen. Number 307 depicts the mechanism in an expanded state 38C 38D. Number 308 depicts the mechanism describe in a folded state 37E 37F. Number 309 depicts a tubular tissue structure or vessel that has been folded parallel to the axis with one fold so that the interior lumen is in intimate contact with the opposing side, such that the vessel is no longer patent, such as sealing closed a fallopian tube 38B. The device would be delivered in a folded state. The device would then be expanded into the lumen of the vessel by the delivery device. The device would then be collapsed or folded this time with tissue engaged in member 310 and captured between the sets of struts 307.

Figure 39:
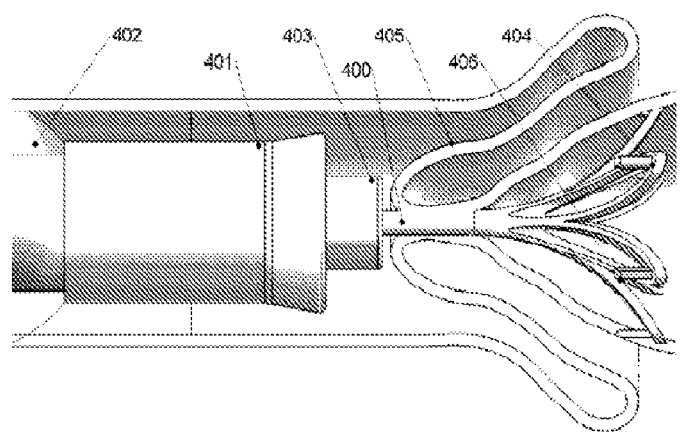
FIG. 39 shows an early stage in the deployment of a device of an embodiment of the invention. A distal anchor element has been advanced expanded to engage the tissue wall, and axially drawn back to create an inverted fold in the tissue wall.
Figure 40:
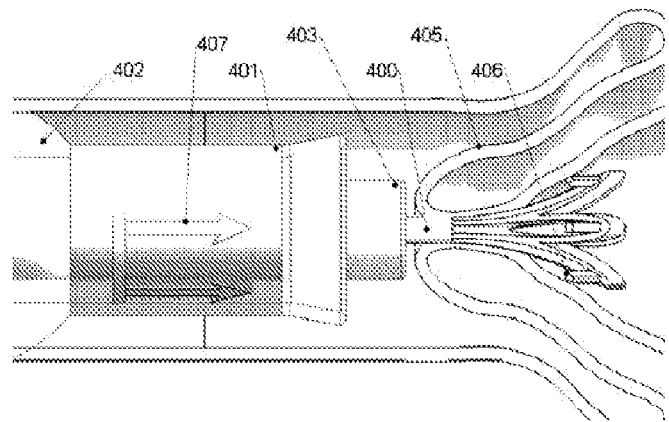
FIG. 40 shows a next step in the deployment shown in FIG. 39 with the tissue further inverted and the members reduced in diameter.
Figure 41:
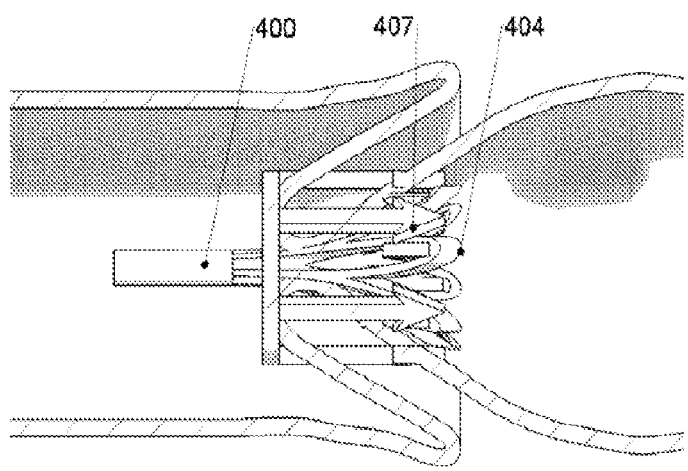
FIG. 41 shows the final implant for the deployment shown in FIGS. 39 and 40, with a proximal member engaging the tissue and distal member.

FIGS. 39, 40, and 41 depict another embodiment of the invention. The invention for closing the lumen of a vessel by substantially inverting the tissue of the lumen and securing it so that it the lumen area is effectively reduced and therefore closes the vessel. The delivery device would be introduced as described previously. A radially expandable distal tissue engagement anchor is deployed into the lumen at the desired location. This member has tissue engagement features or barbs which facilitate the manipulation of the vessel wall tissue. These engagement features would gain purchase on the vessel wall when the distal anchor is axially moved in the direction toward the delivery device or proximally. The distal anchor is then continued to move axially and proximally for distance which would facilitate a folding and then inverting of the vessel wall. This motion will also apply force to the distal anchor structure in a radially compressive manner thus reducing the overall diameter of the member. The delivery device then deploys the proximal anchoring device which engages the tissue that has been inverted, folded, and or twisted and secures it in this configuration effectively closing the lumen of the vessel. The proximal anchor can engage the distal anchor device, achieving the same effect. The devices depicted here are representational; any of the devices already described may achieve this same state of tissue manipulation. Additionally the device shown here can also impart twisting, and plicating the lumen to a closed state.

FIG. 39 depicts the first stage of this inverting deployment. The distal expanding anchor arms 404 are shown expanded. The tissue engagement barbs 406 are engaged into tissue. The distal mechanism was pulled axially toward the delivery system 401 to achieve this tissue engagement, inversion, and plication 405. The delivery system 403 is coupled to and imparts the axial force to the distal anchor 400. The outer portion of the delivery system is stationary and could be temporarily fix by an expanding member 402.

FIG. 40 depicts the expanding members in a constricting state, allowing for the tissue to further invert, twist or plicate. The tissue could even be pulled into the lumen of the catheter. This member could be used in conjunction with any of the previously described features. The proximal engagement feature 407 is retained in the outer member of the delivery system 401. The axial forces applied to the tissue through the distal anchor impart a constrictive radial force to the distal member thus reducing its radial expansion. The next step is for the proximal anchor to be deployed and engaged into the inverted, plicated, and or twisted tissue. The member could also be engaged onto or into the distal anchor in conjunction with or independent of the tissue engagement to secure the closed lumen state.

FIG. 41 depicts an inverted tubular lumen in cross-section being retained in this position with a proximal engagement feature with piercing members 407 and distal anchor mechanism 404. The delivery device was decoupled from the anchor members and removed. The lumen tissue is in intimate contact with itself effectively closing the lumen.

In another embodiment of the present invention, a distal anchor element is advanced into the lumen and expanded to engage the lumen wall. This distal anchor element is then drawn towards a matching proximal cap element which is mounted on the same central shaft. This acts to pull at least one fold of the lumen wall tissue into the cap element and create a seal about the perimeter of the cap against the circumference of the tissue wall of the lumen. The tissue is then retained in this configuration by locking the proximal and distal elements in their axial locations on the central shaft before decoupling the implant from the delivery system.

Figure 42:
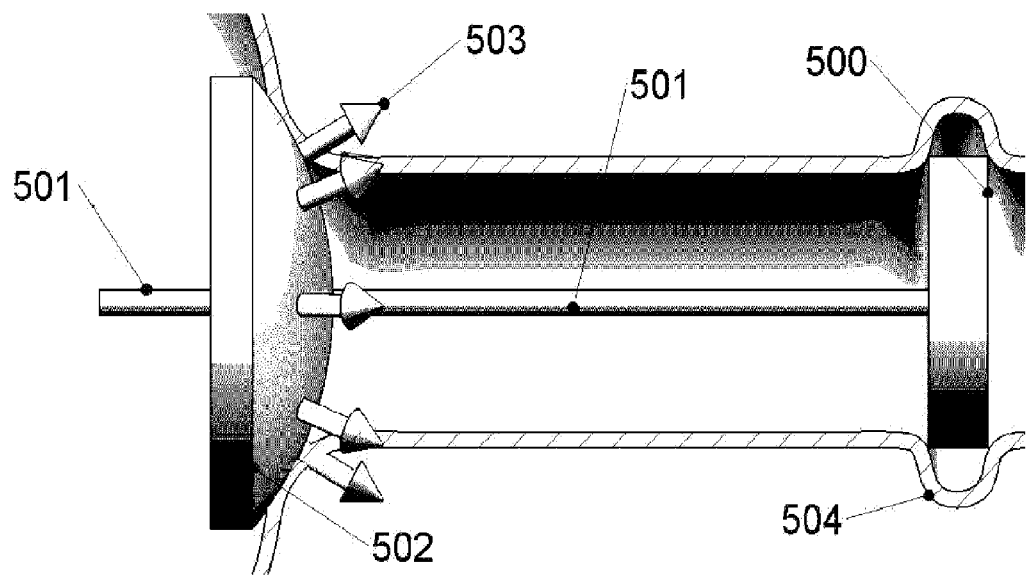
FIG. 42 is a schematic representation of an embodiment of the invention with one of the anchor members being inside the lumen and the second anchor member being in the ostium of the lumen.

In another embodiment of the present invention, the distal anchoring element may be coupled to a proximal anchor element which is not within the lumen but instead seats into or against the ostium of the lumen. One possible embodiment of a proximal anchor is a simple disk sized larger than the diameter of the lumen so that it seats against the ostium. This disk can be smooth or possibly include barbs to help facilitate torsional anchoring if twisting is to be used between the anchoring elements. FIG. 42 depicts a mechanism that can manipulate a tubular tissue structure or vessel such to twist, and/or plicate along the axis so that the interior lumen is in intimate contact with the opposing side, such that the vessel is no longer patent, such as sealing closed a fallopian tube. The assembly of FIG. 42 is similar to that of the previous embodiments with the exception that the proximal member resides in the uterine cavity 505. All previous mechanisms could be utilized in this configuration as the distal mechanism 500. This embodiment benefits from inducing the same mechanism of sterilization as an internal uterine device IUD. This mechanism can be coupled with all of the tissue manipulation techniques described herein also. The proximal uterine mechanism 502 can be passive or can actively engage the tissue with engagement features 503. The structure could be made from any expandable construction and material such as plastic, and or metal. The engagement features could be barbs, hooks, or any shape that facilitates adherence to the tissue by actively piercing, grabbing, or otherwise actively engaging the tissue. The proximal end could have a convex expandable feature which may facilitate better sealing of the passageway. The mechanism is introduced into the fallopian tube in the same manner as previously described. The distal anchor 500 is inserted a distance to where the proximal anchor is seated at the ostium at the uterus. The distal anchor is then deployed and expanded. The tissue is then engaged 504 and manipulated in a desired manner twisted, plicated, folded, any method of reducing the lumen. The proximal anchors presence in the uterus acts as to induce the body's response the same as an IUD and therefore is an effective secondary birth control mechanism. The distal anchor mechanism may be activated by the proximal end of the central member 501 that connects the two ends. This mechanism could be designed to be collapsed and removed, if that feature were desired.

Figure 43:
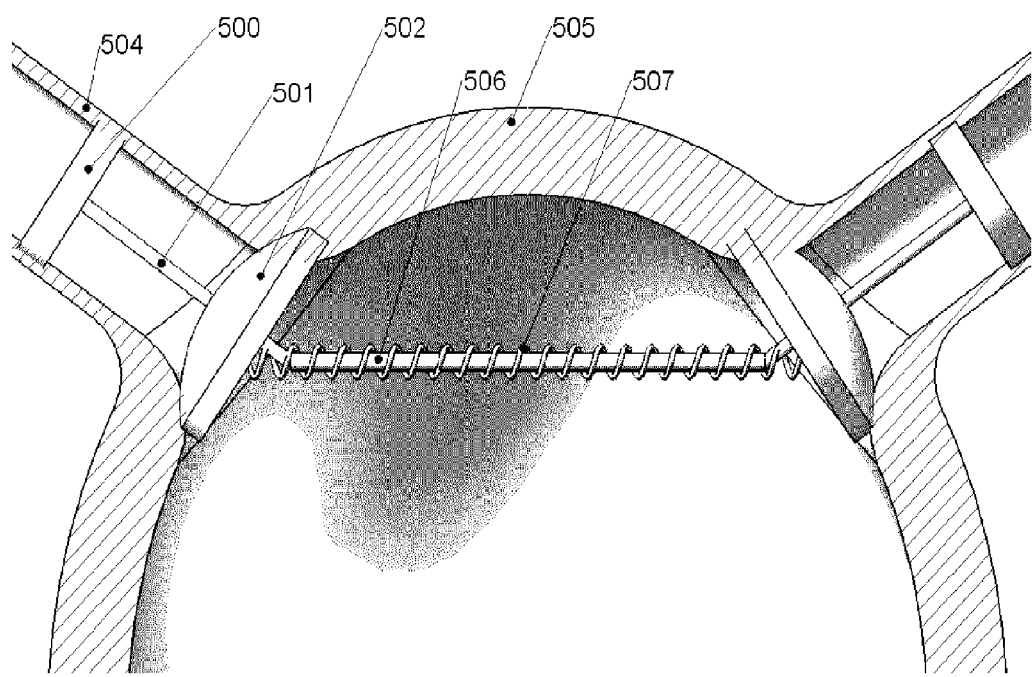
FIG. 43 shows two devices as described in FIG. 42 deployed into the ostia of the fallopian tubes of a patient. The devices are connected with a support element which acts to press the two devices away from each other and into the ostia of the fallopian tubes.

In another embodiment of the invention, the ostial plugs used as the proximal anchor elements in the two fallopian tubes may be coupled with an elastic support element connecting the back of the plug elements through the uterus. A support element such as this may help anchor the individual occluding devices my providing additional compressive force to help maintain engagement of the plug element to the ostium of the fallopian tube. FIG. 43 depicts this embodiment of the invention. This embodiment is the same as FIG. 42 with the addition of a central member that transverses the uterine cavity 505 and is connected to both proximal anchors 502 and associated assemblies 506. This member facilitates the device placement, its permanency and its removal. The member provides a force that prevents the device from falling out unless it is bent away form the axis. This transversing member could provide a passive or an active force against the wall of the uterus. This force could be generated form a mechanism within the transverse central member 507. This member could facilitate a reduction in holding force needed by the distal anchors 500. The central member 501 represented here could be constructed in all the ways previously described herein. The transverse central member 502 and the proximal uterine anchor 502 could be constructed of, coated with, or otherwise consist of materials that act as a birth control mechanism; such as copper, hormones, or any material that induces a response which inhibits pregnancy.

Delivery of a device including the described support element connecting the two ostial plug elements may be done by first deploying the two plug devices separately. Then introducing the support element and connecting it to the backs of the plug elements. This connection can be achieved with a snap in fitting on the end of the support element. The support element length may be selected based on measurement of the patients specific anatomy or by using a telescoping mandrel and tube which can be length adjusted in vivo and locked with a simple ratchet mechanism between the telescoping mandrel and tube.

In another variation on these embodiments, these proximal plug anchor elements may be coated with a material which may be ovacidal or spermicidal or cause tissue irritation or injury such as described earlier.

In another embodiment of the invention, this type of construct could be used without the twisting or bunch/plicating or folding being created between the proximal and distal anchor elements. In this embodiment, a permanent tissue to tissue occlusion of the lumen may not be created and the implant may be used as a removable intra uterine device. The primary method of occluding the lumen in this embodiment is the plugging of the ostia of the fallopian tubes Most or all of the embodiments described above require at least one actuation step by the user to deploy the implant into the desired body lumen. These actuations could take the form of twisting, pulling, pushing, pressurizing or any number of other possible actuation means or combinations of these which are well known to those familiar with catheter or scope design. Some specific actuation methods have been described as examples for some of the embodiments but these are meant to be illustrative examples and not to limit the range of other possible actuation methods.

All of the elements and features of the embodiments described can be used interchangeably and universally to accomplish the said goal of closing the lumen.

Although the invention has been described in terms of particular embodiments and applications, one of ordinary skill in the art, in light of this teaching, can generate additional embodiments and modifications without departing from the spirit of or exceeding the scope of the claimed invention. Accordingly, it is to be understood that the drawings and descriptions herein are proffered by way of example to facilitate comprehension of the invention and should not be construed to limit the scope thereof.

What is claimed is:

1. A method of creating a permanent occlusion at a desired occlusion site in a body lumen comprising:
    inserting a device into the body lumen such that a first element of the device is distal to the desired occlusion site and a second element of the device is proximal to the desired occlusion site;
    actuating the device so as to engage tissue of the lumen with the first element and the second element and to twist the first element relative to the second element to reduce an open area of the lumen between said first and second elements;
    decoupling the implantable device from a delivery system;
    withdrawing the delivery system, leaving the implantable device in the lumen; and
    imaging the tissue after actuating the device and before releasing the implanted device from the delivery system.

2. The device method of claim 1, wherein actuating the device places the device in a first position, the method further comprising reversing the actuation to withdraw the device from the first position and actuating the device again to place the device in a second position.

3. The method of claim 1, wherein the body lumen is a fallopian tube.

4. A method of creating a permanent occlusion at a desired occlusion site in a body lumen comprising:
    inserting a device into the body lumen such that a first element of the device is distal to the desired occlusion site and a second element of the device is proximal to the desired occlusion site;
    actuating the device so as to engage tissue of the lumen with the first element and the second element by radially expanding the first element and the second element, and to twist the first element relative to the second element to reduce an open area of the lumen between said first and second elements; and
    decoupling the implantable device from a delivery system; and
    withdrawing the delivery system, leaving the implantable device in the lumen.

5. The method of claim 4, wherein actuating the device further comprises pulling the first element towards the second element to form a fold in the tissue.

6. The method of claim 4, wherein the body lumen is a fallopian tube.

7. The method of claim 4, further comprising imaging the tissue after actuating the device and before releasing the implanted device from the delivery system.

8. A method of creating a permanent occlusion at a desired occlusion site in a fallopian tube, the method comprising:
    inserting a device into the body lumen such that a first element of the device is distal to the desired occlusion site and a second element of the device is proximal to the desired occlusion site;
    actuating the device so as to engage tissue of the lumen with the first element and the second element and to twist the first element relative to the second element to reduce an open area of the lumen between said first and second elements; and
    decoupling the implantable device from a delivery system; and withdrawing the delivery system, leaving the implantable device in the lumen.

* * * * *